United States Patent

Mayer et al.

Patent Number: 5,434,124
Date of Patent: Jul. 18, 1995

[54] SULFONYLUREA DERIVATIVES AND THEIR USE

[75] Inventors: Horst Mayer, Ludwigshafen; Gerhard Hamprecht, Weinheim; Karl-Otto Westphalen, Speyer; Matthias Gerber, Mutterstadt; Helmut Walter, Obrigheim, all of Germany

[73] Assignee: BASF Aktiengesellschaft, Ludwigshafen, Germany

[21] Appl. No.: 94,178

[22] PCT Filed: Jan. 29, 1992

[86] PCT No.: PCT/EP92/00182
§ 371 Date: Aug. 6, 1993
§ 102(e) Date: Aug. 6, 1993

[87] PCT Pub. No.: WO92/14715
PCT Pub. Date: Sep. 3, 1992

[30] Foreign Application Priority Data

Feb. 22, 1991 [DE] Germany .................. 41 05 518.7

[51] Int. Cl.[6] .................. C07D 239/69; C07D 239/48; A01N 43/54
[52] U.S. Cl. .................. 504/214; 544/321; 544/323; 544/332
[58] Field of Search .................. 504/214; 544/321, 323, 544/332

[56] References Cited

U.S. PATENT DOCUMENTS

| | | | |
|---|---|---|---|
| 4,127,405 | 11/1978 | Levitt | 544/211 |
| 4,435,205 | 3/1984 | Reap | 544/323 |
| 4,515,624 | 5/1985 | Reap | 544/211 |
| 4,534,789 | 8/1985 | Reap | 544/211 |
| 4,576,633 | 3/1986 | Reap | 544/211 |
| 4,835,311 | 5/1989 | Gass et al. | 564/86 |

FOREIGN PATENT DOCUMENTS

| | | |
|---|---|---|
| 0030433 | 6/1981 | European Pat. Off. . |
| 0125205 | 11/1984 | European Pat. Off. . |
| 0135332 | 3/1985 | European Pat. Off. . |
| 0158600 | 10/1985 | European Pat. Off. . |
| 0136061 | 1/1988 | European Pat. Off. . |

Primary Examiner—John M. Ford
Attorney, Agent, or Firm—Oblon, Spivak, McClelland, Maier & Neustadt

[57] ABSTRACT

Sulfonylurea derivatives of the formula I

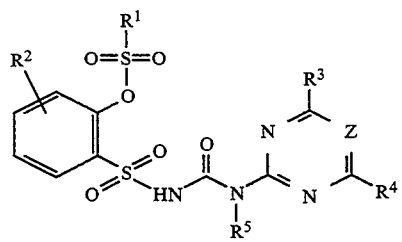

where
$R^1$ is unsubstituted or substituted alkyl or phenyl; alkenyl or propargyl, alkylamino or dialkylamino;
$R^2$ is hydrogen, halogen, unsubstituted or substituted methyl, methoxy or ethoxy, alkylsulfonyl, nitro or cyano;
$R^3$ is difluoromethoxy, trifluoromethoxy, bromodifluoromethoxy, chlorodifluoromethoxy or fluorine;
$R^4$ is halogen, unsubstituted or halogen-substituted methyl, ethyl, methoxy or ethoxy or is methylamino or dimethylamino;
$R^5$ is hydrogen, alkyl or alkenyl or alkynyl, and
Z is CH or N, with the proviso that
a) when $R^3$ is difluoromethoxy, $R^1$ is not dialkylamino, $R^2$ is not alkylsulfonyl and $R^4$ is not methyl or methoxy and
b) when $R^3$ is fluorine and Z is N, $R^4$ is not alkylamino, and salts thereof are suitable as herbicides.

8 Claims, No Drawings

SULFONYLUREA DERIVATIVES AND THEIR USE

This is a 371 of PCT/EP92/00182, filed Jan. 29, 1992.

The present invention relates to substituted sulfonylurea derivatives of the general formula I

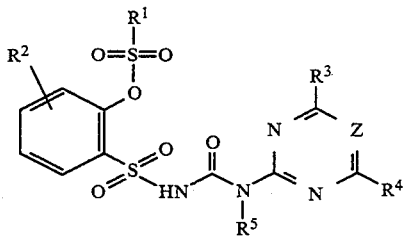

where
- $R^1$ is $C_1$–$C_4$-alkyl which may carry up to three of the following radicals: halogen or $C_1$- or $C_2$-alkoxy; $C_2$- or $C_3$-alkenyl; propargyl; $C_1$–$C_3$-alkylamino; di-$C_1$–$C_4$-alkylamino or phenyl which may carry up to three of the following radicals: halogen, $C_1$–$C_4$-alkyl or $C_1$- or $C_2$-alkoxy;
- $R^2$ is hydrogen, halogen, methyl, methoxy or ethoxy, each of which may carry from 1 to 3 halogen atoms, or $C_1$- or $C_2$-alkylsulfonyl, nitro or cyano;
- $R^3$ is difluoromethoxy, trifluoromethoxy, bromodifluoromethoxy, chlorodifluoromethoxy or fluorine;
- $R^4$ is halogen, methyl, ethyl, $C_1$- or $C_2$-haloalkyl, $C_1$- or $C_2$-haloalkoxy, methoxy, ethoxy, methylamino or dimethylamino;
- $R^5$ is hydrogen, $C_1$–$C_3$-alkyl, $C_2$- or $C_3$-alkenyl or $C_3$- or $C_4$-alkynyl and
- Z is CH or N, with the proviso that
a) if $R^3$ is difluoromethoxy, $R^1$ is not dialkylamino, $R^2$ is not alkylsulfonyl and $R^4$ is not methyl or methoxy and
b) if $R^3$ is fluorine and Z is N, $R^4$ is not alkylamino,
and agriculturally useful salts thereof.

The present invention furthermore relates to processes for the preparation of the stated compounds of the general formula I and to their use as herbicides.

European Patents EP-B 30 433, 44 212, 125 205, 135 332, 136 061 and 158 600 and U.S. Pat. Nos. 4,534,789 and 4,127,405 describe unsubstituted or substituted alkyl- or arylsulfonates and EP-A 125 205 and U.S. Pat. Nos. 4,576,633 and 4,515,624 describe unsubstituted or substituted aminosulfonates based on sulfonylurea, as herbicides. However, they do not meet all requirements with regard to activity and selectivity.

End products of the formula I which are preferred because of the biological activity are those of the formula I where
- $R^1$ is $C_1$–$C_4$-alkyl, such as methyl, ethyl, n-propyl, isopropyl, n-butyl, isobutyl, sec-butyl or tert-butyl, preferably methyl or ethyl,
  $C_1$–$C_3$-haloalkyl, such as fluoromethyl, chloromethyl, bromomethyl, 2-fluoroethyl, 2-chloroethyl, difluoromethyl, dichloromethyl, trifluoromethyl, trichloromethyl, 2,2,2-trifluoroethyl or 2,2,2-trichloroethyl, preferably 2,2,2-trifluoroethyl,
  $C_2$–$C_5$-alkoxyalkyl, such as methoxymethyl, ethoxymethyl, 2-methoxyethyl, 2-ethoxyethyl, 2-methoxypropyl, 3-methoxypropyl, 2-ethoxypropyl or 3-ethoxypropyl, preferably methoxymethyl, ethoxymethyl or 2-methoxyethyl, propargyl,
  $C_2$- or $C_3$-alkenyl, such as vinyl, 1-propen-3-yl or 1-propen-1-yl, preferably vinyl or 1-propen-3-yl,
  $C_1$–$C_3$-alkylamino, such as methyl-, ethyl-, n-propyl- or isopropylamino, preferably methylamino, di-$C_1$–$C_4$-alkyl, such as dimethyl-, diethyl-, di-n-propyl-, di-isopropyl-, di-tert-butyl-, methylethyl- or methylisopropylamino, preferably dimethylamino, aryl, such as phenyl, 2-fluorophenyl, 3-fluorophenyl, 4-fluorophenyl, 2-chlorophenyl, 3-chlorophenyl, 4-chlorophenyl, 2-tolyl, 3-tolyl, 4-tolyl, 2-tert-butylphenyl, 3-tert-butylphenyl, 4-tert-butylphenyl, 2-anisyl, 3-anisyl, 4-anisyl, 2-ethoxyphenyl, 3-ethoxyphenyl or 4-ethoxyphenyl, preferably phenyl, 4-tolyl or 4-anisyl,
- $R^2$ is hydrogen, fluorine, chlorine, bromine, iodine, methyl, methoxy, ethoxy, nitro, cyano, trichloromethyl, trifluoromethyl, methylsulfonyl or ethylsulfonyl, preferably hydrogen, fluorine, chlorine, methyl or methoxy,
- $R^3$ is difluoromethoxy, trifluoromethoxy, chlorodifluoromethoxy or fluorine,
- $R^4$ is fluorine, chlorine, bromine, iodine, methoxy, ethoxy, methyl, ethyl, trifluoromethyl, 1,1,1-trifluoroethyl, difluoromethoxy, trifluoromethoxy, bromodifluoromethoxy, chlorodifluoromethoxy, 2,2,2-trifluoroethoxy, 1,1,2,2-tetrafluoroethoxy, 2-chloro-1,1,2-trifluoroethoxy, methylamino or dimethylamino, preferably methoxy, chlorine, fluorine, methyl, trifluoromethoxy, chlorodifluoromethoxy or trifluoromethyl, and
- $R^5$ is hydrogen, methyl, ethyl, n-propyl, isopropyl, vinyl, 1-propen-3-yl, propargyl or 2-butyn-1-yl, preferably hydrogen, methyl or 1-propen-3-yl.

The novel sulfonylureas of the formula I are obtainable by various methods which are described in the literature. Particularly advantageous methods (A–D) are described in detail below by way of example.

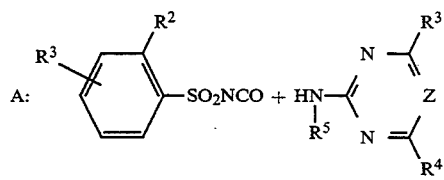

A:

II      III

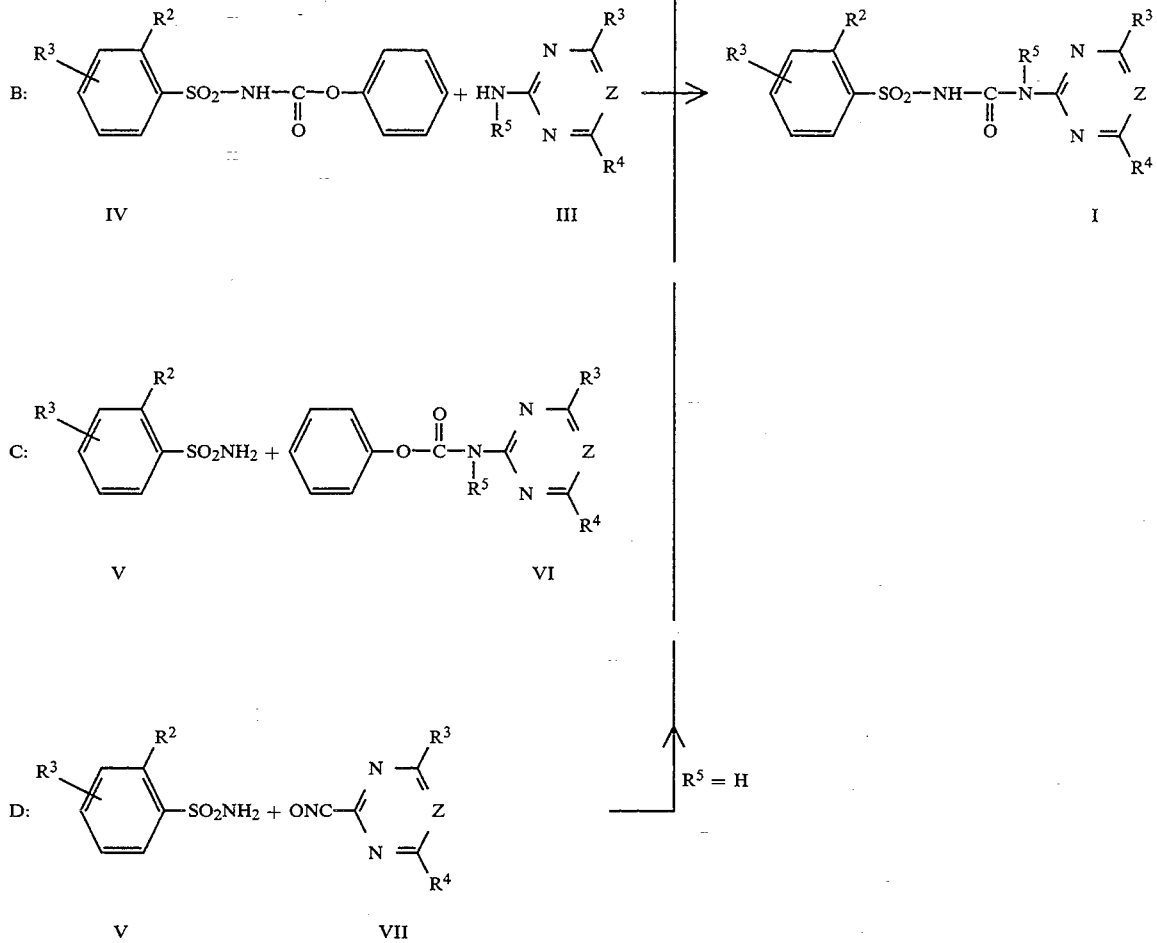

A: A sulfonyl isocyanate II is reacted in a conventional manner (EP-A-162 723 or EP-A-44 212) with about the stoichiometric amount of a 2-amino- 1,3,5-triazine or -pyrimidine derivative III at from 0° to 120° C., preferably from 10° to 100° C. The reaction can be carried out under atmospheric or superatmospheric pressure (up to 50 bar), preferably at from 1 to 5 bar, continuously or batchwise.

Solvents and diluents which are inert under the particular reaction conditions are advantageously used for the reactions. Examples of suitable solvents are halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o-, p- or m-dibromobenzene, o-, m- or p-chlorotoluene, or 1,2,4 -trichlorobenzene, ethers, eg. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole or β,β'-dichlorodiethyl ether, nitrohydrocarbons, such as nitromethane, nitroethane, nitrobenzene, o-, m- or p-chloronitrobenzene or o-nitrotoluene, nitriles, such as acetonitrile, butyronitrile, isobutyronitrile, benzonitrile, m-chlorobenzonitrile, aliphatic or cycloaliphatic hydrocarbons, eg. heptane, pinane, nonane, o-, m- or p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane or octane, esters, eg. ethyl acetate, ethyl acetoacetate or isobutyl acetate, amides, eg. formamide, methylformamide or dimethylformamide, ketones, eg. acetone or methyl ethyl ketone; and corresponding mixtures. Advantageously, the solvent is used in an amount of from 100 to 2,000, preferably from 200 to 700, % by weight, based on the starting material II.

The compound II required for the reaction is generally used in about an equimolar amount (for example from 80 to 120%, based on the particular starting material III). The starting material III in one of the abovementioned diluents may be initially taken and the starting material II then added.

Advantageously, however, the process for the preparation of the novel compounds is carried out by a method in which the starting material II, if necessary in one of the abovementioned diluents, is initially taken and the starting material III then added.

To complete the reaction, stirring is carried out for a further 20 minutes to 24 hours at from 0° to 120° C., preferably from 10° to 100° C., after the addition of the components.

A tertiary amine, eg. pyridine, $\alpha,\beta,\gamma$-picoline, 2,4- or 2,6-lutidine, 2,4,6-collidine, p-dimethylaminopyridine, trimethylamine, triethylamine, tri-n-propylamine, 1,4-diaza[2.2.2]bicyclooctane [DABCO] or 1,8-diazabicyclo[5.4.0]undec-7-ene, in an amount of from 0.01 to 1 mol per mol of starting material II can advantageously be used as a reaction accelerator.

The end substance I is isolated from the reaction mixture in a conventional manner, for example after distilling off solvents or directly by filtering off under suction. The remainder of the residue can be washed with water or dilute acid to remove basic impurities. However, the residue may also be dissolved in a water-immiscible solvent and washed in the manner described. The desired end substances are obtained in pure form; if necessary, they can be purified by recrystallization, stirring in an organic solvent which absorbs the impurities or chromatography.

This reaction is preferably carried out in acetonitrile, methyl tert-butyl ether, toluene or methylene chloride in the presence of from 0 to 100, preferably from 0 to 50, mol equivalents of a tertiary amine, such as 1,4-diazabicyclo[2.2.2]octane or triethylamine.

B: A corresponding sulfonyl carbamate of the formula IV is reacted in a conventional manner (EP-A-120 814, EP-A-101 407) with a 2-amino-1,3,5-triazine or -pyrimidine derivative III in an inert organic solvent at from 0° to 120° C., preferably from 10° to 100° C. Bases such as tertiary amines may be added, with the result that the reaction is accelerated and the product quality is improved.

Examples of suitable bases for this purpose are tertiary amines as stated under A, in particular triethylamine or 1,4-diazabicyclo[2.2.2]octane, in an amount of from 0.01 to 1 mol per mol of starting material IV.

The solvents stated under A are advantageously used. The solvent is employed in an amour of from 100 to 2,000, preferably from 200 to 700, % by weight, based on the starting material IV.

The compound IV required for the reaction is used in general in about an equimolar amount (for example from 80 to 120%, based on the particular starting material III). The starting material IV in one of the abovementioned diluents may be initially taken and the starting material III then added.

However, the starting material III in one of the stated solvents or diluents may also be initially taken and the sulfonyl carbamate IV added.

In both cases, a base can be added as a catalyst, before or during the reaction.

The end product I can be obtained from the reaction mixture in a conventional manner as stated under A.

C: A sulfonamide of the formula V is reacted in a conventional manner (EP-A-141 777 and EP-A-101 670) with about the stoichiometric amount of a phenylcarbamate VI in an inert organic solvent at from 0° to 120° C., preferably from 20° to 100° C. The reaction can be carried out under atmospheric or superatmospheric pressure (up to 50 bar), preferably at from 1 to 5 bar, continuously or batchwise.

Bases such as tertiary amines, which accelerate the reaction and improve the product quality, may be added. Suitable bases for this purpose are those stated under A, in particular triethylamine, 2,4,6-collidine, 1,4-diazabicyclo[2.2.2]octane [DABCO] or 1,8-diazabicyclo[5.4.0]undec-7-ene (DBU), in an amount of from 0.01 to 1 mol per mol of starting material V.

Advantageously used solvents or diluents are those stated under A.

The solvent is used in an amount of from 100 to 2,000, preferably from 200 to 700, % by weight, based on the educt V.

The compound V required for the reaction is used in general in about an equimolar amount (for example from 80 to 120%, based on the particular starting materials VI). The starting material VI in one of the abovementioned diluents may be initially taken and the starting material V then added.

However, the starting material V in one of the stated solvents may also be initially taken and the carbamate VI then added. In both cases, one of the stated bases may be added as a catalyst, before or during the reaction.

To complete the reaction, stirring is carried out for a further 20 minutes to 24 hours at from 0° to 120° C., preferably from 10° to 100° C., in particular from 20° to 80° C., after the addition of the components.

The sulfonylureas of the formula I are isolated from the reaction mixture by a conventional method, as described under A.

D: A sulfonamide of the formula V is reacted in a conventional manner (EP-A-234 352) with about the stoichiometric amount of an isocyanate VII in an inert organic solvent at from 0° to 150° C., preferably from 10° to 100° C. The reaction can be carried out at atmospheric or super-atmospheric pressure (up to 50 bar), preferably at from 1 to 5 bar, continuously or batchwise.

Bases such as tertiary amines, which accelerate the reaction and improve the product quality, can be added before or during the reaction. Suitable bases for this purpose are those stated under A, in particular triethylamine or 2,4,6-collidine, in an amount of from 0.01 to 1 mol per mol of starting material V.

Advantageously used solvents are those stated under A. The solvent is used in an amount of from 100 to 2,000, preferably from 200 to 700, % by weight, based on the educt V.

The compound V required for the reaction is used in general in about an equimolar amount (for example from 80 to 120%, based on the educt VII). The starting material VII in one of the stated diluents may be initially taken and the starting material V then added. However, the sulfonamide can also be initially taken and the isocyanate VII then added.

To complete the reaction, stirring is carried out for a further 20 minutes to 24 hours at from 0° to 120° C., preferably from 10° to 100° C., in particular from 20° to 80° C., after the addition of the components. The end product I can be obtained from the reaction mixture in the conventional manner as described under A.

The sulfonyl isocyanates of the formula II which are required as starting materials can be obtained in a conventional manner from the corresponding sulfonamides by phosgenation (EP-A 44 212, Houben-Weyl 11/2 (1985), 1106, U.S. Pat. No. 4,379,769) or by reacting the sulfonamides with chlorosulfonyl isocyanate (German Laid-Open Application DOS 3,132,944).

The synthesis of the heterocyclic amines of the general formula III and the reactions of the resulting intermediates can be carried out in general by methods such as those described in standard works of heterocyclic literature (Pyrimidines: D. J. Brown in The Chemistry of Heterocyclic Compounds, A. Weissberger and E. C. Taylor (Editors), Wiley, New York, 1985, Vol. 16; D. J. Brown in Comprehensive Heterocyclic Chemistry, A. R. Katritzky (Editor), Pergamon Press, New York, 1984, Vol. 3, 57 et seq.; Triazines: E. M. Smolin and L. Rapoport in The Chemistry of Heterocyclic Compounds, A. Weissberger (Editor), Interscience Publishers, New York, 1959, Vol. 13; J. E. Quirke in Comprehensive Heterocyclic Chemistry, A. R. Katritzky (Editor), Pergamon Press, New York, 1984, Vol. 3, 457 et seq.).

2-Aminopyrimidines and 2-amino-1,3,5-triazines which carry a trifluoromethoxy or chlorodifluoromethoxy radical in the 4- or 6-position can be prepared in particular by the methods of German Applications P 40 07 316.5, P 40 07 317.3, P 40 07 683.0, P 40 24 761.9, P 40 24 755.4 and P 40 24 754.6.

Thus, derivatives of the formula IIIa, where $R^4$ is methylamino, dimethylamino, methoxy, ethoxy or $C_2$-haloalkoxy, can be prepared according to Scheme 2.

thylpyrimidine of the formula XV is reacted according to Scheme 3.

Scheme 3:

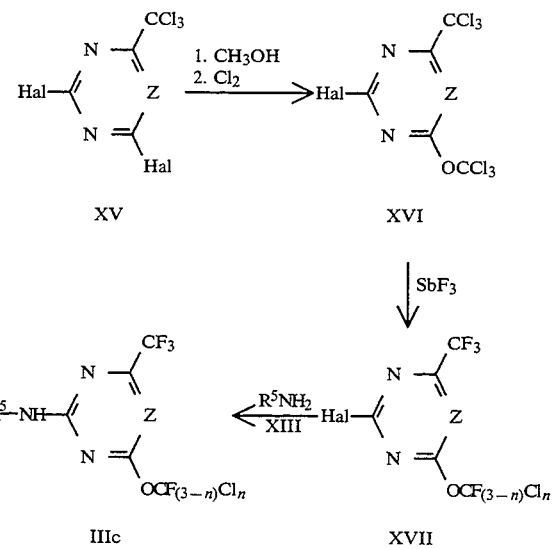

Scheme 2:

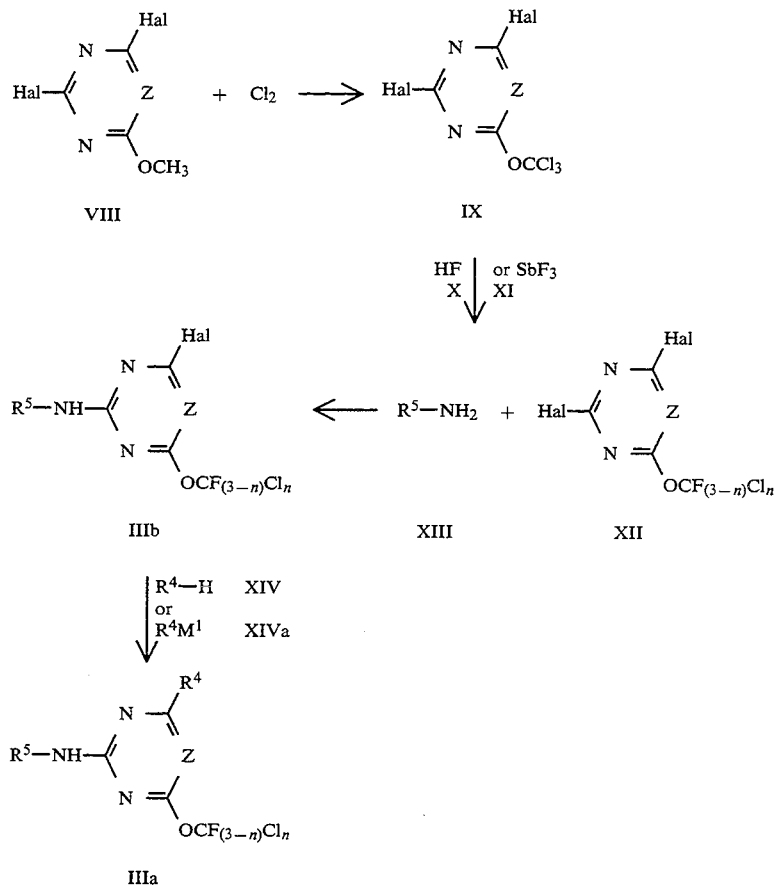

$n=0.1$; $R^4$=NHCH$_3$, N(CH$_3$)$_2$, OCH$_3$, OC$_2$H$_5$ or C$_1$- or C$_2$-haloalkoxy; Z=CH or N The 2-amino-6-trifluoromethyl-1,3,5-triazine or 2-amino-6-trifluoromethylpyrimidine derivatives IIIc are obtained in a similar manner if a 2,4-dihalo-6-trichloromethyl-1,3,5-triazine or 2,4-dihalo-6-trifluorome- The intermediates IIId

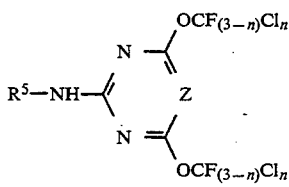

are obtained starting from the intermediates XII in Scheme 2, by substitution of the halogen atom in the 4-position by the reaction sequence described in Scheme 3 (1. CH₃OH, 2. Cl₂, 3. SbF₃) and subsequent reaction with $R^5NH_2$.

4-Alkyl-2-amino-1,3,5-triazines or 4-alkyl-2-aminopyrimidines IIIe are obtained in a similar manner when 2-alkoxy-4-alkyl-6-halotriazines or 4-alkoxy-6-alkyl-2-halopyrimidines are reacted according to Scheme 4.

Scheme 4:

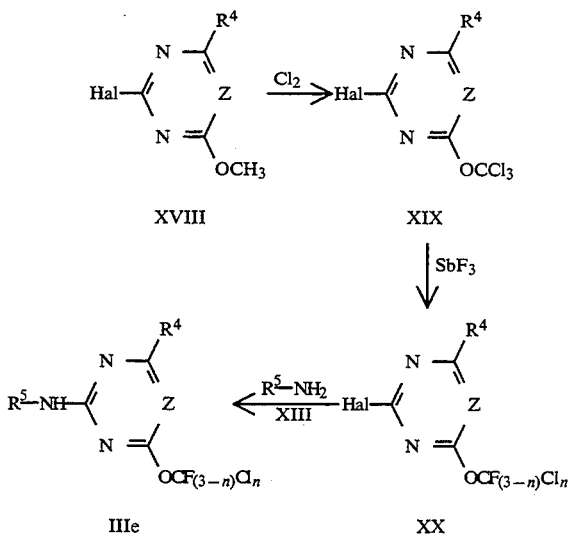

$R^4 = CH_3$ or $C_2H_5$ and $Z = CH$ or $N$

The 2-alkoxy-4-alkyl-6-halo-1,3,5-triazines and 4-alkoxy-6-alkyl-2-halopyrimidines required as starting materials are known from the literature (eg. 2-chloro-4-methoxy-6-methylpyrimidine in Bull. Soc. Chim. Belg. 68 (1959), 30; 2-chloro-4-methoxy-6-methyl-1,3,5-triazine in Monatsh. Chem. 101 (1970), 724) or can be prepared in a similar manner.

The chlorination of the 2-methoxy-1,3,5-triazines or 2-methoxypyrimidines VIII, XV or XVIII with chlorine to give the trichloromethoxy derivatives IX, XVI or XIX is carried out, for example, at from 100° to 180° C.

Suitable chlorinating agents are elemental chlorine or chlorine-donating substances, such as sulfuryl chloride or phosphorus pentachloride.

The reaction can be carried out in the presence of an inert solvent, for example a chlorohydrocarbon, such as chlorobenzene, 1,2-, 1,3- or 1,4-dichlorobenzene, a nitro compound, such as nitrobenzene, a carboxylic acid, such as acetic acid or propionic acid, an anhydride, such as acetic anhydride, an acyl chloride, such as chloroacetyl chloride, α-chloropropionyl chloride or α,α-dichloropropionyl chloride, an inorganic acid halide, such as phosphorus trichloride or phosphorus oxychloride, preferably in the absence of a solvent, in the melt of the starting material VIII, XV or XVIII.

If necessary, the reaction can be accelerated by adding a free radical initiator; suitable ones are exposure to light, preferably UV light, or the addition of α,α'-azoisobutyronitrile, advantageously in an amount of from 0.2 to 7 mol %, based on the starting material VIII, XV or XVIII. The reaction can also be accelerated by adding a catalyst; suitable ones are phosphorus pentachloride, advantageously in an amount of from 0.5 to 7 mol %, based on the starting material VIII, XV or XVIII. In this case, the starting material VIII, XV or XVIII is initially taken together with the catalyst and chlorination is then begun. Instead of the phosphorus pentachloride, a starting component which forms it under the reaction conditions, for example phosphorus trichloride or yellow phosphorus, may also be added and the chlorination then begun.

The starting material VIII, XV or XVIII can be reacted with chlorine in a roughly stoichiometric amount or preferably in excess, advantageously with from 3.1 to 11, in particular from 3.3 to 5, mol of Cl₂ per equivalent of methoxy in the starting materials VIII, XV or XVIII. The reaction can be carried out at from 100° to 180° C., advantageously from 120° to 150° C., under atmospheric or superatmospheric pressure, continuously or batchwise.

If chlorination is carried out at 1 bar, advantageously from 3.3 to 5 mol, based on one equivalent of methoxy in the starting material VIII, XV or XVIII of chlorine gas are used, corresponding to a chlorine conversion of from 91 to 60%. By suitable measures with regard to the apparatus, for example by using moderate superatmospheric pressure, advantageously at from 1 to 10 bar, or by employing a bubble column, the chlorine conversion can be increased. The chlorine gas is advantageously permitted to come into contact with the organic phase for as long as possible, for example by vigorously stirring said phase or making it necessary for the chlorine gas to penetrate a thick layer of the organic phase.

The reaction time is in general about 0.5–12 hours.

In a preferred embodiment of the process, the required amount of chlorine gas is passed into the liquid starting material VIII, XV or XVIII in the course of from 0.5 to 12 hours, preferably from 1 to 10 hours, with thorough stirring, the reaction being started at from 120° to 130° C. and the temperature being increased continuously, possibly utilizing the exothermic nature of the reaction, so that the reaction is carried out at from 135° to 150° C. toward the end. In the case of relatively large reaction batches, the exothermic nature must be taken into account by external cooling or suitable metering of the amount of chlorine; as the reaction proceeds, the cooling bath is removed and, if necessary, further heating can be carried out.

Working up and isolation of the end substances can be carried out in a conventional manner. For example, the residues of hydrogen chloride, chlorine or catalyst can be removed from the hot organic phase by means of an inert gas; a crude product which is already very pure remains behind in high yield. It can be further purified by distillation or chromatography or used directly for further reactions.

The reaction of the trichloromethoxy derivative IX, XVI or XIX with a halogen-exchanging agent is carried out, for example, at from 0° to 180° C.

A suitable halogen-exchanging agent is antimony trifluoride, in the presence or absence of a catalytic amount of an antimony(V) salt or hydrogen fluoride.

An excess of from 1 to 200, preferably from 5 to 25, mol % of antimony trifluoride is advantageously used per equivalent of trichloromethyl. The amount of catalytic antimony(V) salt is from 1 to 20, preferably from 5 to 18, mol % per equivalent of trichloromethyl. The starting material IX, XVI or XIX is preferably metered at from 90° to 130° C. into the mixture of the halogen-exchanging agent, after which the mixture is heated for from 10 to about 240 minutes at from 110° to 180° C. Working up is then carried out by distillation.

However, the reaction can also be carried out continuously, the starting material IX, XVI or XIX being added at from 110° to 180° C. in the course of from 10 to about 240 minutes and at the same time the resulting low boiling end substances XII, XVII or XX being distilled off under reduced pressure. Traces of entrained antimony salts can be eliminated by extraction with concentrated hydrochloric acid.

If the reaction is carried out without catalysis by an antimony(V) salt or only small amounts, for example from 0.5 to 5 mol %, are used, and the amount of antimony trifluoride is reduced to 60–90 mol % per equivalent of trichloromethyl, the halogen exchange stops at the chlorodifluoromethoxy stage.

Instead of antimony trifluoride, halogen exchange can also be carried out using hydrogen fluoride at from 0° to 150° C., preferably from 40° to 120° C. For this purpose, an excess of from 300 to 700, preferably from 350 to 400, mol % of hydrogen fluoride per equivalent of trichloromethyl is added to the starting material IX, XVI or XIX in an autoclave and stirring is carried out for from 10 minutes to 10 hours. If necessary, the reaction can be accelerated in the same manner as described for the use of antimony trifluoride, by adding a catalyst, such as antimony pentachloride. After the pressure has been let down and volatile constituents removed, working up is carried out in the manner described.

The reaction of the fluoromethoxy derivative XII, XVII or XX with the amine XIII is carried out, for example, at from −80° to 40° C.

The 2-halo-1,3,5-triazines or -pyrimidines XII, XVII or XX can be reacted with the amines XIII in an aprotic polar solvent at from −80° to 40° C., either the amine XIII being used in excess or an auxiliary organic base being employed.

The following solvents are suitable for the reaction of the triazines or pyrimidines XII, XVII or XX with the amine XIII: ethers, such as methyl tert-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters, such as ethyl acetate, n-butyl- acetate and isobutyl acetate, and chlorohydrocarbons, such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures of these solvents.

The solvent is advantageously used in an amount of from 100 to 2,000, preferably from 400 to 1,200, % by weight, based on the starting material XII, XVII or XX.

Advantageously, from 1.8 to 2.5, in particular from 1.95 to 2.2, mol equivalent, based on the starting materials XII, XVII or XX, of the amine XIII are added in the course of from 0.5 to 2 hours to a mixture of starting materials XII, XVII or XX in one of the abovementioned solvents at from −80° to 40° C., preferably from −70° to 25° C., stirring is carried out until a reaction is complete, which takes up to 3 hours, and the mixture is then allowed to warm up to 25° C. for working up.

If only about the stoichiometric amount of the amine XIII is used, from 0.9 to 1.1 equivalents, based on the starting material XII, XVII or XX, of an auxiliary organic base are advantageously used. Suitable auxiliary bases are organic bases, such as trimethylamine, triethylamine, N-ethyldiisopropylamine, triisopropylamine, N,N-dimethylaniline, N,N-dimethylcyclohexylamine, N-methylpyrrolidine, pyridine, quinoline, α-, β- and γ-picoline, 2,4- and 2,6-lutidine and triethylenediamine.

The reaction can be carried out under atmospheric or superatmospheric pressure, continuously or batchwise.

Working up is effected by extracting the reaction mixture with water to remove the salts, drying and purifying the organic phase, for example by chromatography. However, it is also possible directly to evaporate down the organic phase and to stir the residue with a solvent.

The 2-amino-4-fluoroalkoxy-1,3,5-triazines or 2-amino-4-fluoroalkoxypyrimidines of the formula IIIa are advantageously obtained by reacting a 2-amino-4-fluoroalkoxy-6-halo-1,3,5-triazine or -pyrimidine of the formula IIIb

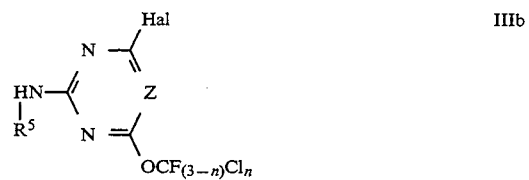

where Hal is fluorine, chlorine or bromine and $R^5$, n and Z have the abovementioned meanings, with a nucleophile of the formula XIV

R⁴—H        XIV where $R^4$ is methylamino, dimethylamino, methoxy, ethoxy or $C_1$- or $C_2$-haloalkoxy, or its salt XIVa.

The reaction of the 2-amino-4-fluoroalkoxy-1,3,5-triazines or 2-amino-4-fluoroalkoxypyrimidines IIIb with a nucleophile XIV or its salt XIVa is carried out, for example, at from −80° to 80° C.

The 4-halo derivatives IIIb can be reacted with the nucleophile XIV or XIVa in an aprotic polar solvent at from −80° to +80° C., advantageously from −30° to +20° C., either the nucleophile being used in excess or an auxiliary organic base being employed.

The following solvents are suitable for the reaction of the 4-halo derivatives IIIb with the nucleophile XIV or XIVa: ethers, such as methyl tert-butyl ether, diethyl ether, ethyl propyl ether, n-butyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters, such as ethyl acetate, n-butyl acetate and isobutyl acetate, and chlorohydrocarbons, such as methylene chloride, 1,1,2,2-tetrachloroethane, 1,1-dichloroethylene, 1,2-dichloroethane, chlorobenzene, 1,2-dichlorobenzene and 1-chloronaphthalene and mixtures of these solvents.

The solvent is advantageously used in an amount of from 100 to 2,000, preferably from 400 to 1,200, % by weight, based on the starting material IIIb.

Advantageously, from 1.8 to 2.5, in particular from 1.95 to 2.2, mol equivalents, based on starting material IIIb, of the nucleophile XIV or XIVa are added in the course of from 0.5 to 2 hours to a mixture of starting material IIIb in one of the abovementioned solvents at from −80° to 80° C., preferably from −30° to 25° C., stirring is carried out until the reaction is complete (for up to 3 hours) and the mixture is then allowed to warm up to 25° C. for working up.

If only about a stoichiometric amount of the nucleophile XIV or XIVa is used, from 0.9 to 1.1 equivalents, based on the starting material IIIb, of an auxiliary organic base must advantageously be added. Suitable auxiliary bases are organic bases, such as trimethylamine, triethylamine, N-ethyldiisopropylamine, triisopropylamine, N,N-dimethylaniline, N,N-dimethylcyclohexylamine, N-methylpyrrolidine, pyridine, quinoline, α-, β- and γ-picoline, 2,4- and 2,6-lutidine and triethylenediamine.

The reaction can be carried out under atmospheric or superatmospheric pressure, continuously or batchwise.

Working up is effected by extracting the reaction mixture with water to remove the salts, drying and purifying the organic phase, for example by chromatography. However, the reaction products are generally sufficiently pure so that it is necessary only to filter off the precipitated salt and to evaporate down the organic phase.

2-Amino- or 2-alkylamino-, 2-alkenylamino- or 2-alkynylamino-substituted pyrimidines which carry a fluorine atom in the 4- or 6-position can be prepared by the process described in EP-A-378 092 or in Yakugaku Zasshi 87 (1967), 1315, or similarly to this process. The corresponding 1,3,5-triazines are obtainable in a similar manner. Suitable intermediates, for example 2,4-difluoro-6-methoxy-1,3,5-triazine, are known from the literature (FR-A 1 561 876 (CA 72, 90530), German Laid-Open Application DOS 2,910,498 (CA 91, 194627) or Chem. Ber. 102 (1969), 2330).

2-Amino- or 2-alkylamino-, 2-alkenylamino- or 2-alkynylamino-substituted pyrimidines or 1,3,5-triazines of the formula III which carry a bromodifluoromethoxy group in the 4- or 6-position are described in EP-A 169 815.

2-Amino- or 2-alkylamino-, 2-alkenylamino- or 2-akynylamino-substituted pyrimidines, which carry a difluoromethoxy group in the 4- or 6-position are obtainable by the methods described in EP-A 84 020.

The sulfonyl carbamates of the formula IV were prepared by reactions known per se (for example EP-A 120 814) or by reactions similar to these. However, the sulfonyl isocyanates of the formula I can also be converted with phenol in a smooth reaction in an inert solvent, such as ether or dichloromethane, into the carbamates of the formula IV.

Carbamates of the formula VI are obtainable by known reactions (for example EP-A 101 670) or by reactions similar to these, but can also be prepared from the corresponding isocyanates VII by reaction with phenol.

The isocyanates of the formula VII are obtained from the amines of the formula III by treatment with oxalyl chloride or phosgene (similarly to Angew. Chem. 83 (1971), 407 or EP-A 388 873).

The sulfonamides of the formula V can be obtained by reacting the corresponding sulfonyl chlorides with ammonia (Houben-Weyl, Methoden der organischen Chemie, 9 (1955), 605). The sulfonyl chlorides are obtained either by a Meerwein reaction (diazotization of suitable amines and sulfochlorination under catalysis with copper salt) or by chlorosulfonation of suitable aromatics (F. Muth in Methoden der organischen Chemie, Houben-Weyl, Thieme-Verlag, Stuttgart (1955), 557 et seq.). The sulfonamides of the formula V can also be prepared from suitably substituted 2-hydroxybenzenesulfonamides by reaction with suitably substituted sulfonyl halides in the presence of an auxiliary base.

Typical examples for the preparation of the intermediates are described in the experimental section.

The salts of the compounds I are obtainable in a conventional manner (EP-A-304 282 or U.S. Pat. No. 4,599,412). They are obtained by deprotonation of the corresponding sulfonylureas I in water or in an inert organic solvent at from −80° to 120° C., preferably from 0° to 60° C., in the presence of a base.

Examples of suitable bases are alkali metal or alkaline earth metal hydroxides, hydrides, oxides or alcoholates, such as sodium, potassium and lithium hydroxide, sodium methylate, ethylate and tert-butylate, sodium and calcium hydride and calcium oxide.

Examples of suitable solvents in addition to water are alcohols, such as methanol, ethanol, and tert-butanol, ethers, such as tetrahydrofuran and dioxane, acetonitrile, dimethylformamide, ketones, such as acetone and methyl ethyl ketone, and halohydrocarbons.

The deprotonation can be carried out at atmospheric pressure or at up to 50 bar, preferably at from atmospheric pressure to 5 bar gage pressure.

The compounds I or the herbicides containing them and their environmentally compatible salts of alkali metals and alkaline earth metals can control weeds very well in crops such as wheat, rice and corn without damaging the crops, an effect which occurs in particular at low application rates. They can be applied, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or oil dispersions. Suitable inert additives include mineral oil fractions having a medium to high boiling point, such as kerosene or diesel oil, as well as coal tar oils and oils of vegetable or animal origin, aliphatic, cyclic and aromatic hydrocarbons, eg. toluene, xylene, paraffin, tetrahydronaphthalene, alkylated naphthalenes or derivates thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates as such or dissolved in an oil or solvent can be homogenized in water by means of wetting agents, adhesives, dispersants or emulsifiers. However, it is also possible to prepare concentrates which consist of active ingredient, wetting agents, adhesives, dispersants or emulsifiers and possibly solvents or oil and which are suitable for dilution with water.

Suitable surfactants are alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkylsulfates, laurylethersulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylarylpolyether alcohols, isotridecyl alcohol, fatty alcohol/ethylene oxide condensates, ethoxylated castor oil, polyoxyethylene alkyl ethers or polyoxypropylene, lauryl alcohol glycol ether acetate, sorbitol esters, ligninsulfite waste liquors or methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flours, bark meal, wood meal and nutshell meal, cellulose powders and other solid carriers.

The formulations contain in general from 0.1 to 95, preferably from 0.5 to 90, % by weight, of active ingredient.

Examples of formulations are:

I. 90 parts by weight of compound No. 1 are mixed with 10 parts by weight of N-methyl-α-pyrrolidone, and a solution which is suitable for use in the form of very small drops is obtained.

II. 20 parts by weight of compound No. 5 are dissolved in a mixture which consists of 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of compound No. 1 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 5 are dissolved in a mixture which consists of 25 parts by weight of cyclohexanone, 65 parts by weight of a mineral oil fraction boiling within the range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

V. 20 parts by weight of active ingredient No. 1 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 14 are mixed with 97 parts by weight of finely divided kaolin. A dusting agent which contains 3% by weight of the active ingredient is obtained in this manner.

VII. 30 parts by weight of active ingredient No. 14 are thoroughly mixed with a mixture of 92 parts by weight of silica gel powder and 8 parts by weight of liquid paraffin, which was sprayed onto the surface of the silica gel. A formulation of the active ingredient having good adhesion is obtained in this manner.

VIII. 20 parts by weight of active ingredient No. 5 are thoroughly mixed with 2 parts by weight of the calcium salt of dodecylbenzenesulfonic acid, 8 parts by weight of fatty alcohol polyglycol ether, 2 parts by weight of the sodium salt of a phenol/urea/formaldehyde condensate and 68 parts by weight of a paraffinic mineral oil. A stable oily dispersion is obtained.

Application may be effected by the preemergence or postemergence method. If the active ingredients are less well tolerated by certain crops, it is possible to use application methods in which the herbicides are sprayed with the aid of the sprayers in such a way that the leaves of the sensitive crops are as far as possible not affected while the active ingredients reach the leaves of undesirable plants growing underneath or the uncovered soil surface (post-directed, lay-by).

The application rates of active ingredient are from 0.001 to 1.0, preferably from 0.01 to 0.5, kg/ha of active ingredient (a.i.), depending on the purpose of control, the season, the target plants and the stage of growth.

In view of the versatility of the application methods, the novel compounds or agents containing them can be used in a further number of crops for eliminating undesirable plants, Examples of suitable crops are:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris spp. altissima* | sugarbeets |
| *Beta vulgaris spp. rapa* | fodder beets |
| *Brassica napus var. napus* | rapeseed |
| *Brassica napus var. napobrassica* | swedes |
| *Brassica apa var. silvestris* | beets |
| *Camellia sinensis* | tea plants |
| *Carthamus tinctorius* | safflower |
| *Citrus limon* | lemons |
| *Citrus sinensis* | orange trees |
| *Coffea arabica (Coffea canephora, Coffea liberica)* | coffee plants |
| *Cucumis sativus* | cucumbers |
| *Cynodon dactylon* | Bermudagrass in turf |

| Botanical name | Common name |
| --- | --- |
| | and lawns |
| *Daucus carota* | carrots |
| *Elaeis guineensis* | oil palms |
| *Fragaria vesca* | strawberries |
| *Glycine max* | soybeans |
| *Gossypium hirsutum* | cotton |
| (*Gossypium arboreum* | |
| *Gossypium herbaceum* | |
| *Gossypium vitifolium*) | |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus spp.* | apple trees |
| *Manihot esculenta* | cassava |
| *Medicago sativa* | alfalfa (lucerne) |
| *Musa spp.* | banana plants |
| *Nicotiana tabacum* | tobacco |
| (*N. rustica*) | |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus spp.* | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*s. vulgare*) | sorghum |
| *Theobroma cacao* | cacao plants |
| *Trifolium pratense* | red clover |
| *Triticum aestivum* | wheat |
| *Triticum durum* | durum wheat |
| *Vicia faba* | tick beans |
| *Vitis vinifera* | grapes |
| *Zea mays* | Indian corn, sweet corn, maize |

To extend the action spectrum and to achieve synergistic effects, the sulfonylurea derivatives of the formula I can be mixed and applied together with a large number of members of other groups of herbicidal or growth-regulating active ingredients. For example, suitable components of the mixture are diazine, 4H-3,1-benzoxazine derivatives, benzothiadiazinones, 2,6-dinitroanilines, N-phenylcarbamates, thiocarbamates, halocarboxylic acids, triazines, amides, ureas, diphenyl ether, triazinones, uracils, benzofuran derivatives, cyclohexane-1,3-dione derivatives, quinolinecarboxylic acid derivatives, phenyloxy- or hetaryloxy-phenylpropionic acids and their salts, esters and amides and others.

It may also be useful if the compounds of the formula I, alone or in combination with other herbicides, are mixed, and applied together with, further crop protection agents, for example with pesticides or agents for controlling phytopathogenic fungi or bacteria. The miscibility with mineral salt solutions used for eliminating nutrient and trace element deficiencies is also of interest. Nonphytotoxic oils and oil concentrates can also be added.

Examples of the synthesis of the compounds I are described below.

PREPARATION OF THE PRECURSORS

2-Amino-4-chlorophenyl methanesulfonate 174.5 g (1.52 mol) of methanesulfonyl chloride were added dropwise at 10°–15° C. to a solution of 218.7 g (1.52 mol) of 2-amino-4-chlorophenol and 153.8 g (1.52 mol) of triethylamine in 400 ml of methylene chloride. The mixture was stirred for 18 hours at 25° C. and was introduced into ice water, and the organic phase was separated off, washed twice with water and dried over $Na_2SO_4$. After the solvent had been distilled off, a gradually crystallizing residue of the product remained, which was sufficiently pure for further reaction (329.5 g, 98% of theory). The product could be recrystallized from methanol/water (mp. 70°–71° C.).

$^1$H-NMR spectrum (250 MHz, $CDCl_3$, int. TMS): 7.10 d (1H), 6.75 d (1H), 6.67 dd (1H), 4.10 br (2H), 3.16 s (3H).

2-Chlorosulfonylphenyl methanesulfonate

A diazonium salt solution, prepared by simultaneously introducing a solution of 39.5 g (0.57 mol) of sodium nitrite in 60 ml of water and 105 g (0.57 mol) of 2-aminophenyl methanesulfonate into 200 ml of concentrated hydrochloric acid at 0°–5° C. and stirring for 1 hour at 0° C., was added dropwise at 0°–10° C. to a solution, saturated with sulfur dioxide, of 1.7 g of $CuCl_2$ and 4.5 g of benzyltriethylammonium chloride in 200 ml of 1,2-dichloroethane and 10 ml of water. The means of cooling were removed and stirring was carried out for 30 minutes at 25° C. and then, while slowly increasing the temperature of the reaction mixture, for a further hour at 50° C. The organic phase was separated off, washed with ice water and dried over $Na_2SO_4$. After removal of the solvent, an oily residue remained and could be crystallized by trituration with a little methanol. This gave 139 g (90% of theory) of the title compound of melting point 94°–95° C.

$^1$H-NMR (300 MHz, $CDCl_3$, int. TMS): 8.10 d (1H), 7.68–7.85 m (2H), 7.51 (1H), 3.42 s (3H).

2-Aminosulfonylphenyl methanesulfonate

Ammonia was passed at −30° C. into a solution of 130.3 g of 2-chlorosulfonylphenyl methanesulfonate in 1 l of tetrahydrofuran, and the conversion was checked by thin-layer chromatography. After the reaction was complete, the tetrahydrofuran was distilled off under reduced pressure from a water pump and the residue was triturated with water and diethyl ether. This gave 110.2 g (91%) of the title compound of melting point 131°–132° C.

$^1$H-NMR (300 MHz, $CD_3SOCD_3$, int. TMS): 7.90 d (1H), 7.61 br (2H), 7.45–7.74 m (3H), 3.50 s (H).

2-(Dimethylaminosulfonyloxy)-benzenesulfonamide 4.0 g (29 mmol) of potassium carbonate were added to a solution of 5.0 g (29 mmol) of 2-hydroxybenzenesulfonamide in 200 ml of acetonitrile at 25° C. Stirring was carried out for 10 minutes, after which 4.1 g (29 mmol) of dimethylaminosulfonyl chloride were added dropwise at 25° C. and stirring was continued for a further 16 hours at this temperature. The volatile constituents were removed under reduced pressure from a water pump, the residue was taken up in ethyl acetate, the solution was dried over $Na_2SO_4$ and the solvent was removed under reduced pressure from a water pump. The remaining residue was stirred vigorously for 1 hour with 100 ml of diethyl ether. The crystalline product was filtered off under suction and dried at 40° C. under reduced pressure. 5.7 g of the title compound were obtained in this manner.

$^1$H-NMR spectrum (250 MHz, CD$_3$SOCD$_3$, int. TMS, δ): 7.91 d (1H); 7.57–7.74 m (2H); 7.49 br (2H); 7.36–7.52 m (1H); 3.02 s (6H).

PREPARATION OF THE INTERMEDIATES III

2,4-Difluoro-6-trichloromethoxy-1,3,5-triazine

A stream of chlorine gas was passed into a mixture of 300 g (2.041 mol) of 2,4-difluoro-6-methoxy-1,3,5-triazine and 0.3 g of α,α'-azoisobutyronitrile at 130° C. and with exposure to UV light, so that a temperature of 140°–145° C. was established for 2 hours. After the progress of the reaction had been checked by NMR spectroscopy, chlorine gas was passed in for a further 3 hours with external heating at from 135° to 140° C. The precipitate which had separated out was filtered off under suction and the filtrate was distilled under reduced pressure to give 444 g (87% of theory) of the title compound of boiling point 40°–46° C./0.3 mbar.

2,4-Difluoro-6-trifluoromethoxy-1,3,5-triazine

Half of 210 g (0.838 mol) of 2,4-difluoro-6-trichloromethoxy-1,3,5-triazine was added to a mixture of 187.4 g (1.048 mol) of antimony trifluoride and 35.2 g (0.117 mol) of antimony pentachloride, initially at 110° C. while stirring, so that a temperature of 125° C. was first established; with the resulting reflux, external heating was necessary on further addition. Stirring was carried out for one hour at 125°–130° C. and a fraction boiling at from 100° to 105° C. was distilled off over a 25 cm packed column. After the reaction had ceased, the remaining half of the trichloromethoxy compound was added dropwise in the course of 30 minutes, and the fraction passing over at from 100° to 105° C. was distilled off continuously. The total reaction time was 3 hours. 134.4 g (79.8% of theory) of the title compound with $n_D^{24} = 1.3650$ were obtained.

6-Chlorodifluoromethoxy-2,4-difluoro-1,3,5-triazine 210 g (0.838 mol) of 2,4-difluoro-6-trichloromethoxy-1,3,5-triazine were added to 110 g (0.614 mol) of antimony trifluoride in the course of 10 minutes while stirring at 110° C. After the addition of ¾ of 9.38 g (0.0313 mol) of antimony pentachloride, the mixture was heated to 145° C. and stirred for 1 hour. The remaining catalyst was added and stirring was continued for a further 2 hours, 20 g (11.8% of theory) of 2,4-difluoro-6-trifluoromethoxy-1,3,5-triazine being obtained as a low boiling fraction over a 30 cm packed column at from 95° to 105° C. The distillation residue was distilled without a column and gave 94.8 g (52% of theory) of the title compound of boiling point 125°–130° C. and $n_D^{24} = 1.4042$.

2,4-Dichloro-6-trifluoromethoxy-1,3,5-triazine 52 g (0.183 mol) of 2,4-dichloro-6-trichloromethoxy-1,3,5-triazine were added to a mixture of 40.9 g (0.229 mol) of antimony trifluoride and 7.03 g (0.0234 mol) of antimony pentachloride in the course of 5 minutes while stirring at 90° C., the temperature increasing to 180° C. Stirring was continued for 20 minutes at from 170° to 180° C. after which the crude product was distilled off at 90°–103° C./70 mbar. Further distillation gave 32.3 g (75.5% of theory) of the title compound of boiling point 165°–173° C.

2-Amino-4-fluoro-6-trifluoromethoxy-1,3,5-triazine 4.4 g (0.259 mol) of ammonia gas were passed into a mixture of 26.0 g (0.1293 mol) of 2,4-difluoro-6-trifluoromethoxy-1,3,5-triazine in 100 ml of tetrahydrofuran in the course of 45 minutes at from −70° to −65° C. while stirring. Stirring was carried out for 2 hours at −70° C. and overnight while the mixture warmed up to 22° C. The mixture was evaporated down under reduced pressure, after which the residue was stirred with water, filtered off under suction and washed. Drying gave 22 g (85.9% of theory) of the title compound of melting point 138°–139° C.

2,4-Bismethylamino-6-trifluoromethoxy-1,3,5-triazine and 2-methylamino-4-fluoro-6-trifluoromethoxy-1,3,5-triazine 5.9 g (0.189 mol) of gaseous methylamine were passed into a mixture of 19.0 g (0.0945 mol) of 2,4-difluoro-6-trifluoromethoxy-1,3,5-triazine in 100 ml of diethyl ether at −70° C. in the course of 30 minutes while stirring. Stirring was carried out for 2 hours at −70° C. and overnight while the mixture warmed up to 22° C. The reaction mixture was evaporated down under reduced pressure, the residue was taken up in methylene chloride and the solution was washed with water. After it had been dried, it was chromatographed over a silica gel column, 5.0 g (25% of theory) of 2-methylamino-4-fluoro-6-trifluoromethoxy-1,3,5-triazine of melting point 68°–72° C. being obtained in the first two fractions. In the further fractions 4–7, 10.7 g (51% of theory) of the more sparingly soluble 2,4-bismethylamino-6-trifluoromethoxy-1,3,5-triazine of melting point 150°–152° C. were isolated.

2-Amino-4-chlorodifluoromethoxy-6-fluoro-1,3,5-triazine and 2,4-diamino-6-chlorodifluoromethoxy-1,3,5-triazine 7.8 g (0.46 mol) of ammonia were passed into a mixture of 50.0 g (0.23 mol) of 2,4-difluoro-6-chlorodifluoromethoxy-1,3,5-triazine in 150 ml of tetrahydrofuran in the course of 45 minutes at −70° C. while stirring. Stirring was carried out for 2 hours at −70° C. and overnight while the mixture warmed up to 22° C. The reaction mixture was evaporated down under reduced pressure and the residue was washed with water and dried. The reaction product was then suspended in methylene chloride, the suspension was applied to a silica gel column and elution was carried out with the same solvent. 21.5 g (43.6% of theory) of 2-amino-4-fluoro-6-chlorodifluoromethoxy-1,3,5-triazine of melting point 131°–133° C. were obtained in fractions 1 to 8. By further eluting with ethyl acetate, the more sparingly soluble 2,4-diamino-6-chlorodifluoromethoxy-1,3,5-triazine (11.2 g, 23% of theory) of melting point 114° C. was then isolated in fractions 9 to 14.

2-Chlorodifluoromethoxy-4-fluoro-6-methylamino-1,3,5-triazine and 2,4-bismethylamino-6-chlorodifluoromethoxy-1,3,5-triazine 5.2 g (0.166 mol) of methylamine were passed into a mixture of 18.1 g (0.083 mol) of 4-difluorochloromethoxy-2,6-difluoro-1,3,5-triazine in the course of 20 minutes at −70° C. while stirring. Stirring was carried out for 2 hours at −70° C. and overnight while the mixture warmed up to 22° C. The reaction mixture was evaporated down under reduced pressure, and the residue was taken up in methylene chloride and the solution was washed with water and dried. Chromatography over silica gel gave 5.5 g (29% of theory) of 2-chlorodifluoromethoxy-4-fluoro-6-methylamino-1,3,5-triazine of melting point 62°–64° C. in the first fractions. 8.7 g (44% of theory) of 2,4-bismethylamino-6-chlorodifluoromethoxy-1,3,5-triazine of melting point 118°–120° C. were isolated from subsequent fractions.

2-Amino-4-methoxy-6-trifluoromethoxy-1,3,5-triazine 9.1 g (0.05 mol) of 30% strength sodium methylate were added to a mixture of 10 g (0.05 mol) of 2-amino-4-fluoro-6-trifluoromethoxy-1,3,5-triazine in 100 ml of methanol at 0° C. in the course of 15 minutes while stirring. Stirring was continued for one hour at 0° C., after which the mixture was evaporated down under reduced pressure, the residue was taken up in methylene chloride and the solution was extracted with water. Drying and evaporating down gave 10.5 g (99% of theory) of the title compound of melting point 96°–101° C.

2-Amino-4-chlorodifluoromethoxy-6-methoxy-1,3,5-triazine 8.4 g (0.047 mol) of 30% strength sodium methylate were added to a mixture of 10 g (0.047 mol) of 2-amino-4-chlorodifluoromethoxy-6-fluoro-1,3,5-triazine in 100 ml of methanol at 0° C. in the course of 15 minutes while stirring. Stirring was continued for one hour at 0° C. after which the mixture was evaporated down under reduced pressure, the residue was taken up in methylene chloride and the solution was extracted with water. Drying and evaporating down gave 10.4 g (98.5% of theory) of the title compound of melting point 109°–110° C.

2-Amino-4-methoxy-6-trifluoromethoxy-1,3,5-triazine 9.1 g (0.05 mol) of 30% strength sodium methylate were added to a mixture of 10 g (0.05 mol) of 2-amino-4-fluoro-6-trifluoromethoxy-1,3,5-triazine in 100 ml of methanol at 0° C. in the course of 15 minutes while stirring. Stirring was carried out for one hour at 0° C., after which the mixture was evaporated down under reduced pressure, the residue was taken up in methylene chloride and the solution was extracted with water. Drying and evaporating down gave 10.5 g (99% of theory) of the title compound of melting point 96°–101° C.

2-Amino-4-chlorodifluoromethoxy-6-methoxy-1,3,5-triazine 8.4 g (0.047 mol) of 30% strength sodium methylate were added to a mixture of 10 g (0.047 mol) of 2-amino-4-chlorodifluoromethxoy-6-fluoro-1,3,5-triazine in 100 ml of methanol at 0° C. in the course of 15 minutes while stirring. Stirring was carried for one hour at 0° C., after which the mixture was evaporated down under reduced pressure, the residue was taken up in methylene chloride and the solution was extracted with water. Drying and evaporating down gave 10.4 g (98.5% of theory) of the title compound of melting point 109°–111° C.

2-Amino-4-ethoxy-6-trifluoromethoxy-1,3,5-triazine 2.3 g (0.093 mol) of 97% strength sodium hydride were added a little at a time to 300 ml of ethanol at from 20° to 35° C., and stirring was carried out until a solution was obtained, which took 15 minutes. 18.5 g (0.093 mol) of 2-amino-4-fluoro-6-trifluoromethoxy-1,3,5-triazine were then added at 0° C. in the course of 10 minutes while stirring, and stirring was continued for one hour at 0° C. and overnight at 22° C. The mixture was evaporated down under reduced pressure, after which the residue was taken up in methylene chloride and the solution was extracted with water and dried. Evaporating down gave 17.9 g (85.9% of theory) of the title compound of melting point 69°–91° C.

2-Amino-4-chlorodifluoromethoxy-6-ethoxy-1,3,5-triazine 1.2 g (0.047 mol) of 97% strength sodium hydride were added a little at a time to 150 ml of ethanol at from 20° to 35° C., and stirring was carried out until a solution was obtained, which took 15 minutes. 10.0 g (0.047 mol) of 2-amino-4-chlorodifluoromethoxy-6-fluoro-1,3,5-triazine were then added at 0° C. while stirring, and stirring was continued for one hour at 0° C. and overnight at 22° C. The mixture was evaporated down under reduced pressure, after which the residue was taken up in methylene chloride and the solution was extracted with water and dried. Evaporating down gave 10.6 g (94.6% of theory) of the title compound of melting point 63°–65° C.

2-Amino-4-methylamino-6-trifluoromethoxy-1,3,5-triazine 3.5 g (0.111 mol) of gaseous methylamine were passed into a solution of 11 g (0.055 mol) of 2-amino-4-fluoro-6-trifluoromethoxy-1,3,5-triazine in 150 ml of tetrahydrofuran at 0° C. in the course of 20 minutes while stirring. Stirring was continued for one hour at 0° C. and overnight at 22° C. The reaction mixture was evaporated down under reduced pressure and the residue was stirred with water and dried. 10.8 g (93.1% of theory) of the title compound of melting point 155°–157° C. (decomposition) were obtained.

2-Amino-4-chlorodifluoromethoxy-6-methylamino-1,3,5-triazine 2.9 g (0.093 mol) of gaseous methylamine were passed into a solution of 10 g (0.047 mol) of 2-amino-4-chlorodifluoromethoxy-6-fluoro-1,3,5-triazine in 150 ml of diethyl ether in the course of 20 minutes at 0° C. while stirring. Stirring was continued for one hour at 0° C. and overnight at 22° C. Washing with water, drying and evaporating down gave 9.4 g (89.5% of theory) of the title compound of melting point 143° C. (decomposition).

2-Amino-4-dimethylamino-6-trifluoromethoxy-1,3,5-triazine 5.0 g (0.111 mol) of gaseous dimethylamine were passed into a solution of 11 g (0.055 mol) of 2-amino-4-fluoro-6-trifluoromethoxy-1,3,5-triazine in 150 ml of tetrahydrofuran in the course of 20 minutes at 0° C. while stirring. Stirring was continued for one hour at 0° C. and overnight at 22° C. Evaporating down, washing with water and drying gave 9.9 g (80.7% of theory) of the title compound of melting point 114°–118° C. (decomposition).

2-Amino-4-chlorodifluoromethoxy-6-dimethylamino-1,3,5-triazine 4.2 g (0.093 mol) of dimethylamine were passed into a solution of 10 g (0.047 mol) of 2-amino-4-chlorodifluoromethoxy-6-fluoro-1,3,5-triazine in 150 ml of diethyl ether in the course of 20 minutes at 0° C. while stirring. Stirring was continued for one hour at 0° C. and overnight at 22° C. Washing with water, drying and evaporating down gave 9.8 g (87.8% of theory) of the title compound of melting point 130°–133° C. (decomposition).

2-Chloro-4-trichloromethoxy-6-trichloromethylpyrimidine a) 2-Chloro-4-methoxy-6-trichloromethylpyrimidine 293.1 g (1.692 mol) of a 30% strength sodium methylate solution were added to a solution of 434 g (1.692 mol) of 2,6-dichloro-4-trichloromethylpyrimidine in 1 l of 1,2-dichloroethane in the course of 1½ hours at from 0° to 5° C. while stirring. Stirring was continued for 1 hour at from 0° to 5° C. and for 12 hours at 25° C. The reaction mixture was extracted 4 times with water and 3 times with saturated sodium chloride solution. Drying over magnesium sulfate and evaporating down gave 423 g (95% of theory) of the title compound as a virtually colorless oil.

$^1$H-NMR (CDCl$_3$) (ppm) OCH$_3$ (s/3H) 4.1; CH (s/1H) 7.25.

b) 2-Chloro-4-trichloromethoxy-6-trichloromethylpyrimidine

Chlorine was passed, initially at 110° C. into a mixture of 210 g (0.802 mol) of 2-chloro-4-methoxy-6-trichloromethylpyrimidine and 260 mg (0.0016 mol) of α,α'-azoisobutyronitrile with exposure to UV light and monitoring of the course of the reaction by gas chromatography, the resulting reaction temperature being 140° C. even after the heating bath had been removed. After the reaction had ceased, a total of 341 g (4.8 mol) of chlorine were passed in at 120° C. in the course of 5½ hours. 70 ml of n-pentane were stirred into the cooling reaction mixture from 40° C. to effect precipitation. The precipitate was filtered off under suction, washed with petroleum ether and dried, 163 g (55% of theory) of the title compound of melting point 67°–69° C. being obtained.

According to the gas chromatogram, the filtrate (113.8 g) consisted of 83% of the title compound, 4% of 2-chloro-4-dichloromethoxy-6-trichloromethylpyrimidine and 9% of 2,4-dichloro-6-trichloromethylpyrimidine. The total yield of the title compound was 87.6% of theory.

2,4-Difluoro-6-trichloromethoxypyrimidine 210 g (2.96 mol) of chlorine were passed, with exposure to UV light and monitoring of the course of the reaction under gas chromatography into 123 g (0.843 mol) of 2,4-difluoro-6-methoxypyrimidine, which was prepared by the process described in EP-A 378 089, at 130° C. in the course of 2½ hours while stirring. The reaction mixture was distilled under reduced pressure over a 10 cm Vigreux column, 190.2 g (90.5% of theory) of the title compound of boiling point 40°–43° C./0.2 mbar being obtained.

2,4-Dichloro-6-trichloromethoxypyrimidine 303 g (4.27 mol) of chlorine were passed into a mixture of 209 g (1.168 mol) of 2,6-dichloro-4-methoxypyrimidine and 2 g (0.012 mol) of α,α'-azoisobutyronitrile for ½ hour at 80° C., 1 hour at 100° C., 3 hours at 120° C. and 3 hours at 150° C., while stirring, exposing to UV light and monitoring of the course of the reaction by gas chromatography. The reaction mixture was then distilled under reduced pressure. 241.3 g (73% of theory) of the title compound of boiling point 87°–88° C./0.4 mbar and melting point 55°–56° C. were obtained.

2,4-Difluoro-6-trifluoromethoxypyrimidine 49.9 g (0.2 mol) of 2,4-difluoro-6-trichloromethoxypyrimidine were added to a mixture of 39.3 g (0.22 mol) of antimony trifluoride and 9.38 g (0.031 mol) of antimony pentachloride at 100° C. in the course of 15 minutes while stirring.

The bath temperature was increased to 100°–150° C. in the course of 25 minutes and stirring was continued for 30 minutes, reflux being established at from 120° to 125° C. Subsequent distillation gave 37.1 g (92.7% of theory) of the title compound of boiling point 125°–127° C.

6-Chlorodifluoromethoxy-2,4-difluoropyrimidine 93 g (0.373 mol) of 2,4-difluoro-6-trichloromethoxypyrimidine were added to a mixture of 44.5 g (0.249 mol) of antimony trifluoride and and 0.94 g (0.0031 mol) of antimony pentachloride at 100° C. in the course of 10 minutes while stirring. The bath temperature was increased from 100° to 175° C. in the course of 25 minutes, the reflux being established at 145° C. Stirring was carried out for 1½ hours, after which the reaction product was distilled off at 146°–150° C. The distillate was dissolved in methylene chloride and the solution was extracted with 6N hydrochloric acid and dried over magnesium sulfate. Evaporating down under reduced pressure gave the title compound as a residue, in a yield of 63.7 g (=78.8% of theory).

2-Fluoro-4-trifluoromethoxy-6-trifluoromethylpyrimidine 80 g (0.219 mol) of 2-chloro-4-trichloromethyl-6-trichloromethoxypyrimidine were added to a mixture of 93.9 g (0.525 mol) of antimony trifluoride and 18.7 g (0.0627 mol) of antimony pentachloride in the course of 5 minutes at 100° C. while stirring. The bath temperature was increased to 140° C. in the course of 10 minutes and stirring was continued for 1 hour, vigorous reflux being established. The reaction product was distilled over at 135°–140° C., and toward the end at 95° C./50 mbar. The distillate was taken up in methylene chloride and the solution was extracted over 6N hydrochloric acid and dried over magnesium sulfate. Evaporating down under reduced pressure gave the title compound in a yield of 35.9 g (65.5% of theory).

2,4-Dichloro-6-trifluoromethoxypyrimidine 115 g (0.407 mol) of 2,4-dichloro-6-trichloromethoxypyrimidine were added to a mixture of 80 g (0.447 mol) of antimony trifluoride and 18.77 g (0.0627 mol) of antimony pentachloride in the course of 5 minutes at 100° C. while stirring, the reaction temperature increasing to 140° C. Stirring was continued for a further 45 minutes at 150° C. A pressure of 210 mbar was established for distillation, the title compound passing over at 128° C.; the final volatile constituents were forced over at 110° C./22 mbar. The distillate was dissolved in methylene chloride and the solution was extracted with 6N hydrochloric acid and dried over magnesium sulfate. Evaporating down under reduced pressure gave the title compound in a yield of 80 g (84.4% of theory) as a colorless oil of $n_D^{25}=1.4604$.

2-Amino-4-chlorodifluoromethoxy-6-fluoropyrimidine 9.8 g (0.578 mol) of gaseous ammonia were passed into a mixture of 62.5 g (0.289 mol) of 2,4-difluoro-6-chlorodifluoromethoxypyrimidine in 300 ml of tetrahydrofuran at from $-75°$ to $-70°$ C. in the course of one hour while stirring. Stirring was continued for one hour at $-70°$ C., after which the mixture was warmed up to room temperature. The precipitate which had separated out was filtered off under suction and partitioned between ethyl acetate and water and the organic phase was dried over mangesium sulfate. The reaction filtrate was evaporated down, the residue was dissolved in the above ethyl acetate phase, the solution was chromatographed over silica gel using 5:1 petroleum ether/ether and the eluate was evaporated down. 46.5 g (75.3% of theory) of the title compound were obtained as colorless crystals of melting point 77°–80° C.

2-Amino-4-fluoro-6-trifluoromethoxypyrimidine 8.7 g (0.51 mol) of gaseous ammonia were passed into a mixture of 51 g (0.255 mol) of 2,4-difluoro-6-trifluoromethoxypyrimidine in 200 ml of diethyl ether in the course of 1 hour at from $-75°$ to $-70°$ C. while stirring. Stirring was continued for a further 1½ hours at $-70°$ C. and for 1 hour at room temperature. The reaction mixture was evaporated down under reduced pressure and the residue was taken up in methylene chloride and extracted with water. Drying the organic phase, evaporating down and chromatographing the residue over silica gel using 8:1 petroleum ether/ether gave 38.1 g (75.6% of theory) of the title compound as colorless crystals of melting point 86°–89° C.

2-Amino-4-chloro-6-trifluoromethoxypyrimidine 4.3 g (0.25 mol) of gaseous ammonia were passed into a mixture of 23.3 g (0.1 mol) of 2,4-dichloro-6-trifluoromethoxypyrimidine in 150 ml of methyl tert-butyl ether in the course of 45 minutes at from $-50°$ to $-45°$ C. while stirring. Stirring was continued for 30 minutes at $-50°$ C., one hour at $-30°$ C. and one hour at 25° C. The precipitate which had separated out was filtered off under suction, washed with water and dried, 5.4 g (33.1% of theory) of 4-amino-2,4-dichloropyrimidine of melting point 270°–272° C. being obtained as a by-product. The filtrate was washed with water, dried, partially evaporated down under reduced pressure and chromatographed using 5:1 petroleum ether/ether, 3 g (12.8% of theory) of starting material being obtained as a colorless oil in the first fractions and 9 g (42% of theory) of the title compound being obtained as colorless crystals of melting point 55°–56° C. in the subsequent fraction. The conversion was 48.3%.

4-Chlorodifluoromethoxy-6-fluoro-2-methylaminopyrimidine 20.3 g (0.0938 mol) of 4-chlorodifluoromethoxy-2,6-difluoropyrimidine in 150 ml of tetrahydrofuran were initially taken and 5.8 g (0.188 mol) of gaseous methylamine were added at from $-70°$ to $-60°$ C. in the course of 30 minutes while stirring. Stirring was carried out for 1 hour at $-70°$ C., for 1 hour at 0° C. and for 1 hour at 25° C. After the reaction mixture had been evaporated down under reduced pressure, the residue was stirred with water and extracted twice with ethyl acetate, and the extract was dried over magnesium sulfate. It was partially evaporated down under reduced pressure and then chromatographed over silica gel using 1:5 ether/petroleum ether. The first fractions contained the title compound of melting point 57°–61° C. in a yield of 12.5 g (58.5%).

2-Amino-4-trifluoromethoxy-6-trifluoromethylpyrimidine 4.7 g (0.278 mol) of gaseous ammonia were passed into a mixture of 38.0 g (0.147 mol) of 2-fluoro(chloro)-4-trifluoromethoxy-6-trifluoromethylpyrimidine in 150 ml of diethyl ether in the course of 1 hour at from $-75°$ to $-70°$ C. while stirring. Stirring was continued for 2 hours at $-75°$ C. and for 2 hours after warming up to 25° C. The precipitate which had separated out was filtered off under suction, after which the organic phase was extracted with water, dried and partially evaporated down. Chromatography over silica gel using methyl tert-butyl ether gave 20.4 g (56.1% of theory) of the title compound of melting point 47°–49° C.

2-Amino-4-methoxy-6-trifluoromethoxypyrimidine 2.7 g (0.015 mol) of 30% strength sodium methylate were added to 2.95 g (0.015 mol) of 2-amino-4-fluoro-6-trifluoromethoxypyrimidine in 50 ml of methanol in the course of 15 minutes at from $-5°$ to 0° C. while stirring. The reaction mixture was stirred for 1 hour at 0° C., warmed up to 25° C. and then evaporated down under reduced pressure, and the residue was stirred with water and extracted twice with methylene chloride. Drying and evaporating down under reduced pressure gave 3.1 g (98% of theory) of the title compound of $n_D^{25}=1.4770$.

2-Amino-4-chlorodifluoromethoxy-6-methoxypyrimidine 26.1 g (0.145 mol) of 30% strength sodium methylate were added to 31.0 g (0.145 mol) of 2-amino-4-chlorodifluoromethoxy-6-fluoropyrimidine in 300 ml of methanol in the course of 15 minutes at $-10°$ to 0° C. while stirring. Stirring was continued for 30 minutes at 0° C. and for 1 hour at 25° C. The reaction mixture was evaporated down under reduced pressure and worked up as described above. 31.6 g (96.6% of theory) of the title compound were obtained as a colorless oil of $n_D^{22}=1.5039$.

4-Chlorodifluoromethoxy-2-methylamino-6-methoxypyrimidine 4.7 g (0.026 mol) of 30% strength sodium methylate were added to 6.0 g (0.0263 mol) of 4-chlorodifluoromethoxy-6-fluoro-2-methylaminopyrimidine in 100 ml of methanol in the course of 10 minutes at 0° C. while stirring. Stirring was continued for 1 hour at 0° C. and for 1 hour at 25° C. Working up in a conventional manner gave 6.3 g (100% of theory) of the title compound of melting point 49°–53° C.

4-Chlorodifluoromethoxy-6-dimethylamino-2-methylaminopyrimidine 1.9 g (0.0417 mol) of gaseous dimethylamine were passed into a mixture of 8.9 g (0.0417 mol) of 2-amino-4- chlorodifluoromethoxy-6-fluoropyrimidine in 100 ml of tetrahydrofuran in the course of 10 minutes at 0° C. while stirring. Stirring was continued for 1 hour at 0° C. and for 2 hours at 25° C. Working up in the conventional manner gave 9.7 g (97.5% of theory) of the title compound of melting point 127°–130° C.

PREPARATION OF THE END PRODUCTS I

1.

2-[[(4-Methoxy-6-trifluoromethoxypyrimidin-2-yl)aminocarbonyl]-aminosulfonyl]-phenylmethanesulfonate 4 g (14 mmol) of 2-isocyanatosulfonylphenyl methanesulfonate were added to a solution of 3 g (14 mmol) of 2-amino-4-methoxy-6-trifluoromethoxypyrimidine in 10 g of 1,2-dichloroethane at 25° C. Stirring was carried out for 10 minutes and the solvent was removed in 1:1 (v/v) ether/pentane. The crystalline product was filtered off under suction and dried at 40° C. under reduced pressure from a water pump. 5 g (73% of theory) of the title compound of melting point 146°–149° C. were thus obtained.

2.

2-[[(4-Fluoro-6-methoxypyrimidin-2-yl)-aminocarbonyl]-aminosulfonyl]-phenyl methanesulfonate 4 g (14 mmol) of 2-isocyanatosulfonylphenyl methanesulfonate were added to a suspension of 2 g (14 mmol) of 2-amino-4-methoxy-6-trifluoromethoxypyrimidine in 10 g of 1,2-dichloroethane at 25° C. A homogeneous solution was formed, from which a bulky, white precipitate separated out after about 30 minutes. The product was filtered off under suction, washed with a little 1,2-dichloroethane and dried at 40° C. under reduced pressure from a water pump. 2 g (34% of theory) of the title compound of melting point 168°–169° C. were obtained in this manner.

3. Sodium salt of 2-[[(4-methoxy-6-trifluoromethoxy-1,3,5-triazin-2-yl)-aminocarbonyl]-aminosulfonyl]-phenyl methanesulfonate 1.1 g (6.2 mmol) of a 30% strength by weight solution of sodium methylate in methanol were added to a solution of 3 g (6.2 mmol) of 2-[[(4-methoxy-6-trifluoromethoxy-1,3,5-triazin-2-yl)-aminocarbonyl]-aminosulfonyl]-phenyl methanesulfonate in 30 ml of methanol at 25° C. Stirring was carried out for 2 minutes at 25° C. and the solvent was removed at 80° C. under reduced pressure from a water pump. The title compound, which decomposed at 130°–135° C., was obtained in quantitative yield in this manner.

The active ingredients stated in Table 1 below were obtained by a similar method of preparation.

TABLE 1

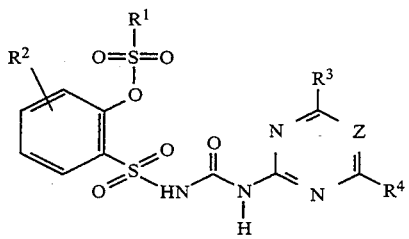

| No. | $R^1$ | $R^2$ | $R^3$ | $R^4$ | Z | mp. [°C.] |
|---|---|---|---|---|---|---|
| 1 | $CH_3$ | H | $OCH_3$ | $OCF_3$ | CH | 146–149 |

TABLE 1-continued

| No. | $R^1$ | $R^2$ | $R^3$ | $R^4$ | Z | mp. [°C.] |
|---|---|---|---|---|---|---|
| 2 | $CH_3$ | H | $OCH_3$ | $OCF_3$ | CH | 184–187* |
| 3 | $CH_3$ | H | $OCH_3$ | $OCF_2Cl$ | CH | 158–160 |
| 4 | $CH_3$ | H | $OCH_3$ | $OCF_2Cl$ | CH | 175–177* |
| 5 | $CH_3$ | H | $OCH_3$ | F | CH | 168–169 |
| 6 | $CH_3$ | H | $OCH_3$ | F | CH | 203–205* |
| 7 | $CH_3$ | H | $OCH_3$ | $OCF_3$ | N | 150–151 |
| 8 | $CH_3$ | H | $OCH_3$ | $OCF_3$ | N | 130–135* |
| 9 | $CH_3$ | H | $OCHF_2$ | $OCHF_2$ | CH | 199–200* |
| 10 | $CH_3$ | H | F | $OCF_3$ | CH | 178–179 |
| 11 | $N(CH_3)_2$ | H | $OCH_3$ | F | CH | >200* |
| 12 | $CH_3$ | 5-Cl | $OCH_3$ | $OCF_3$ | CH | 131–133 |
| 13 | $CH_3$ | 5-Cl | F | $OCF_3$ | CH | >200 |
| 14 | $N(CH_3)_2$ | H | $OCH_3$ | $OCF_3$ | CH | 136–138 |
| 15 | $CH_3$ | 5-$CH_3$ | F | $OCH_3$ | CH | 192–194 |
| 16 | $CH_3$ | 5-$CH_3$ | $OCH_3$ | $OCF_3$ | CH | 122–126 |
| 17 | $CH_3$ | 5-$CH_3$ | F | $OCF_3$ | CH | 179–181 |
| 18 | $CH_3$ | 5-$CH_3$ | F | $OCF_3$ | CH | 140–143* |
| 19 | $CH_3$ | 5-$CH_3$ | F | $OCF_3$ | CH | 137–140** |
| 20 | $CH_3$ | 5-$CH_3$ | $OCH_3$ | $OCF_3$ | CH | 126–128** |
| 21 | $CH_3$ | 5-$CH_3$ | $OCH_3$ | F | CH | 180–195** |
| 22 | $CH_3$ | 5-$CH_3$ | $OCH_3$ | F | CH | 146–150* |
| 23 | $CH_3$ | 5-$CH_3$ | $OCH_3$ | $OCF_3$ | CH | 133–136* |
| 24 | $CH_3$ | H | F | $OCF_3$ | CH | 115–118* |
| 25 | $CH_3$ | H | F | $OCF_3$ | CH | 112–115** |
| 26 | $CH_3$ | 5-Cl | $OCH_3$ | $OCF_3$ | CH | 111–122* |
| 27 | $CH_3$ | 5-Cl | F | $OCF_3$ | CH | 120–125* |
| 28 | $CH_3$ | 5-Cl | F | $OCF_3$ | CH | 122–133** |
| 29 | $C_2H_5$ | H | F | $OCH_3$ | CH | 124–127 |
| 30 | $C_2H_5$ | H | $OCH_3$ | $OCF_3$ | CH | 157–160 |
| 31 | $C_2H_5$ | H | F | $OCF_3$ | CH | 119–122 |
| 32 | $C_2H_5$ | H | $OCH_3$ | $OCF_3$ | CH | 140–142* |
| 33 | $C_2H_5$ | H | F | $OCH_3$ | CH | 118–123* |
| 34 | $N(CH_3)_2$ | H | F | $OCF_3$ | CH | 128–135 |

*Na salt
**K salt

Examples of further herbicidal sulfonylurea derivatives I which are obtainable in a similar manner are shown in Table 2 below. The simplified formulae I' and I''

$$A_{x-y}-SO_2-NH-CO-NH-T_n \qquad I'$$

$$A_{x-y}-SO_2-NH-CO-NH-P_n \qquad I''$$

in which $A_{x-y}$ is an aromatic radical of the formula

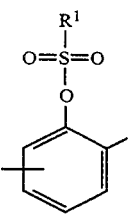

the variable x denotes the radical $R^1$ and the variable y denotes the radical $R^2$ were used here. The meanings are as follows:

| x | R¹ | y | R² |
|---|---|---|---|
| 1 | $CH_3$ | 1 | H |
| 2 | $C_2H_5$ | 2 | 3-F |
| 3 | $n-C_3H_7$ | 3 | 5-F |
| 4 | $i-C_3H_7$ | 4 | 6-F |
| 5 | $n-C_4H_9$ | 5 | 3-Cl |
| 6 | $i-C_4H_9$ | 6 | 5-Cl |
| 7 | $s-C_4H_9$ | 7 | 6-Cl |
| 8 | $t-C_4H_9$ | 8 | $3-OCH_3$ |
| 9 | $CF_3$ | 9 | $5-OCH_3$ |
| 10 | $ClCH_2$ | 10 | $6-OCH_3$ |
| 11 | $CH_3OCH_2$ | 11 | $3-CH_3$ |
| 12 | $NHCH_3$ | 12 | $5-CH_3$ |
| 13 | $NHC_2H_5$ | 13 | $6-CH_3$ |
| 14 | $N(CH_3)_2$ | | |
| 15 | $N(C_2H_5)_2$ | | |
| 16 | Phenyl | | |
| 17 | 2-F-Phenyl | | |
| 18 | 3-F-Phenyl | | |
| 19 | 4-F-Phenyl | | |
| 20 | 2-Cl-Phenyl | | |
| 21 | 3-Cl-Phenyl | | |
| 22 | 4-Cl-Phenyl | | |
| 23 | $2-CH_3$-Phenyl | | |
| 24 | $3-CH_3$-Phenyl | | |
| 25 | $4-CH_3$-Phenyl | | |
| 26 | $2-t-C_4H_9$-Phenyl | | |
| 27 | $3-t-C_4H_9$-Phenyl | | |
| 28 | $4-t-C_4H_9$-Phenyl | | |
| 29 | $2-OCH_3$-Phenyl | | |
| 30 | $3-OCH_3$-Phenyl | | |
| 31 | $4-OCH_3$-Phenyl | | |

Pn and Tn are the pyrimidine or 1,3,5-triazine radicals. The meanings are as follows:

| n | R³ | R⁴ |
|---|---|---|
| 1 | F | F |
| 2 | F | Cl |
| 3 | F | $OCH_3$ |
| 4 | F | $OC_2H_5$ |
| 5 | F | $CH_3$ |
| 6 | F | $C_2H_5$ |
| 7 | F | $CF_3$ |
| 8 | F | $OCF_3$ |
| 9 | F | $OCF_2Cl$ |
| 10 | F | $OCF_2H$ |
| 11 | F | $N(CH_3)_2$ |
| 12 | $OCF_3$ | F |
| 13 | $OCF_3$ | Cl |
| 14 | $OCF_3$ | $OCH_3$ |
| 15 | $OCF_3$ | $OC_2H_5$ |
| 16 | $OCF_3$ | $CH_3$ |
| 17 | $OCF_3$ | $C_2H_5$ |
| 18 | $OCF_3$ | $CF_3$ |
| 19 | $OCF_3$ | $OCF_3$ |
| 20 | $OCF_3$ | $OCF_2Cl$ |
| 21 | $OCF_3$ | $OCF_2H$ |
| 22 | $OCF_3$ | $NHCH_3$ |
| 23 | $OCF_3$ | $N(CH_3)_2$ |
| 24 | $OCF_2Cl$ | F |
| 25 | $OCF_2Cl$ | Cl |
| 26 | $OCF_2Cl$ | $OCH_3$ |
| 27 | $OCF_2Cl$ | $OC_2H_5$ |
| 28 | $OCF_2Cl$ | $CH_3$ |
| 29 | $OCF_2Cl$ | $C_2H_5$ |
| 30 | $OCF_2Cl$ | $CF_3$ |
| 31 | $OCF_2Cl$ | $OCF_3$ |
| 32 | $OCF_2Cl$ | $OCF_2Cl$ |
| 33 | $OCF_2Cl$ | $OCF_2H$ |
| 34 | $OCF_2Cl$ | $NHCH_3$ |
| 35 | $OCF_2Cl$ | $N(CH_3)_2$ |
| 36 | $OCF_2Br$ | F |
| 37 | $OCF_2Br$ | Cl |
| 38 | $OCF_2Br$ | $OCH_3$ |
| 39 | $OCF_2Br$ | $OC_2H_5$ |
| 40 | $OCF_2Br$ | $CH_3$ |
| 41 | $OCF_2Br$ | $C_2H_5$ |
| 42 | $OCF_2Br$ | $CF_3$ |
| 43 | $OCF_2Br$ | $OCF_3$ |
| 44 | $OCF_2Br$ | $OCF_2Cl$ |
| 45 | $OCF_2Br$ | $OCF_2H$ |
| 46 | $OCF_2Br$ | $NHCH_3$ |
| 47 | $OCF_2Br$ | $N(CH_3)_2$ |
| 48 | $OCF_2H$ | F |
| 49 | $OCF_2H$ | Cl |
| 50 | $OCF_2H$ | $OC_2H_5$ |
| 51 | $OCF_2H$ | $C_2H_5$ |
| 52 | $OCF_2H$ | $CF_3$ |
| 53 | $OCF_2H$ | $OCF_3$ |
| 54 | $OCF_2H$ | $OCF_2Cl$ |
| 55 | $OCF_2H$ | $OCF_2H$ |
| 56 | $OCF_2H$ | $NHCH_3$ |
| 57 | $OCF_2H$ | $N(CH_3)_2$ |

TABLE 2

Sulfonylurea I' and II''
$A_{z-y}-SO_2-NH-CO-NH-P_n$ and
$A_{z-v}-SO_2-NH-CO-NH-T_n$

| $A_{x-y}$ | $P_n/T_n$ | $A_{x-y}$ | $P_n/T_n$ | $A_{x-y}$ | $P_n/T_n$ |
|---|---|---|---|---|---|
| 1-1 | 1 | 1-2 | 1 | 1-3 | 1 |
| 1-1 | 2 | 1-2 | 2 | 1-3 | 2 |
| 1-1 | 3 | 1-2 | 3 | 1-3 | 3 |
| 1-1 | 4 | 1-2 | 4 | 1-3 | 4 |
| 1-1 | 5 | 1-2 | 5 | 1-3 | 5 |
| 1-1 | 6 | 1-2 | 6 | 1-3 | 6 |
| 1-1 | 7 | 1-2 | 7 | 1-3 | 7 |
| 1-1 | 8 | 1-2 | 8 | 1-3 | 8 |
| 1-1 | 9 | 1-2 | 9 | 1-3 | 9 |
| 1-1 | 10 | 1-2 | 10 | 1-3 | 10 |
| 1-1 | 11 | 1-2 | 11 | 1-3 | 11 |
| 1-1 | 12 | 1-2 | 12 | 1-3 | 12 |
| 1-1 | 13 | 1-2 | 13 | 1-3 | 13 |
| 1-1 | 14 | 1-2 | 14 | 1-3 | 14 |
| 1-1 | 15 | 1-2 | 15 | 1-3 | 15 |
| 1-1 | 16 | 1-2 | 16 | 1-3 | 16 |
| 1-1 | 17 | 1-2 | 17 | 1-3 | 17 |
| 1-1 | 18 | 1-2 | 18 | 1-3 | 18 |
| 1-1 | 19 | 1-2 | 19 | 1-3 | 19 |
| 1-1 | 20 | 1-2 | 20 | 1-3 | 20 |
| 1-1 | 21 | 1-2 | 21 | 1-3 | 21 |
| 1-1 | 22 | 1-2 | 22 | 1-3 | 22 |
| 1-1 | 23 | 1-2 | 23 | 1-3 | 23 |
| 1-1 | 24 | 1-2 | 24 | 1-3 | 24 |
| 1-1 | 25 | 1-2 | 25 | 1-3 | 25 |
| 1-1 | 26 | 1-2 | 26 | 1-3 | 26 |
| 1-1 | 27 | 1-2 | 27 | 1-3 | 27 |
| 1-1 | 28 | 1-2 | 28 | 1-3 | 28 |
| 1-1 | 29 | 1-2 | 29 | 1-3 | 29 |
| 1-1 | 30 | 1-2 | 30 | 1-3 | 30 |
| 1-1 | 31 | 1-2 | 31 | 1-3 | 31 |
| 1-1 | 32 | 1-2 | 32 | 1-3 | 32 |
| 1-1 | 33 | 1-2 | 33 | 1-3 | 33 |
| 1-1 | 34 | 1-2 | 34 | 1-3 | 34 |
| 1-1 | 35 | 1-2 | 35 | 1-3 | 35 |
| 1-1 | 36 | 1-2 | 36 | 1-3 | 36 |
| 1-1 | 37 | 1-2 | 37 | 1-3 | 37 |
| 1-1 | 38 | 1-2 | 38 | 1-3 | 38 |
| 1-1 | 39 | 1-2 | 39 | 1-3 | 39 |

TABLE 2-continued

Sulfonylurea I' and II''
$A_{z-y}-SO_2-NH-CO-NH-P_n$ and
$A_{z-y}-SO_2-NH-CO-NH-T_n$

| $A_{x-y}$ | $P_n/T_n$ | $A_{x-y}$ | $P_n/T_n$ | $A_{x-y}$ | $P_n/T_n$ |
|---|---|---|---|---|---|
| 1-1 | 40 | 1-2 | 40 | 1-3 | 40 |
| 1-1 | 41 | 1-2 | 41 | 1-3 | 41 |
| 1-1 | 42 | 1-2 | 42 | 1-3 | 42 |
| 1-1 | 43 | 1-2 | 43 | 1-3 | 43 |
| 1-1 | 44 | 1-2 | 44 | 1-3 | 44 |
| 1-1 | 45 | 1-2 | 45 | 1-3 | 45 |
| 1-1 | 46 | 1-2 | 46 | 1-3 | 46 |
| 1-1 | 47 | 1-2 | 47 | 1-3 | 47 |
| 1-1 | 48 | 1-2 | 48 | 1-3 | 48 |
| 1-1 | 49 | 1-2 | 49 | 1-3 | 49 |
| 1-1 | 50 | 1-2 | 50 | 1-3 | 50 |
| 1-1 | 51 | 1-2 | 51 | 1-3 | 51 |
| 1-1 | 52 | 1-2 | 52 | 1-3 | 52 |
| 1-1 | 53 | 1-2 | 53 | 1-3 | 53 |
| 1-1 | 54 | 1-2 | 54 | 1-3 | 54 |
| 1-1 | 55 | 1-2 | 55 | 1-3 | 55 |
| 1-1 | 56 | 1-2 | 56 | 1-3 | 56 |
| 1-1 | 57 | 1-2 | 57 | 1-3 | 57 |
| 1-4 | 1 | 1-5 | 1 | 1-6 | 1 |
| 1-4 | 2 | 1-5 | 2 | 1-6 | 2 |
| 1-4 | 3 | 1-5 | 3 | 1-6 | 3 |
| 1-4 | 4 | 1-5 | 4 | 1-6 | 4 |
| 1-4 | 5 | 1-5 | 5 | 1-6 | 5 |
| 1-4 | 6 | 1-5 | 6 | 1-6 | 6 |
| 1-4 | 7 | 1-5 | 7 | 1-6 | 7 |
| 1-4 | 8 | 1-5 | 8 | 1-6 | 8 |
| 1-4 | 9 | 1-5 | 9 | 1-6 | 9 |
| 1-4 | 10 | 1-5 | 10 | 1-6 | 10 |
| 1-4 | 11 | 1-5 | 11 | 1-6 | 11 |
| 1-4 | 12 | 1-5 | 12 | 1-6 | 12 |
| 1-4 | 13 | 1-5 | 13 | 1-6 | 13 |
| 1-4 | 14 | 1-5 | 14 | 1-6 | 14 |
| 1-4 | 15 | 1-5 | 15 | 1-6 | 15 |
| 1-4 | 16 | 1-5 | 16 | 1-6 | 16 |
| 1-4 | 17 | 1-5 | 17 | 1-6 | 17 |
| 1-4 | 18 | 1-5 | 18 | 1-6 | 18 |
| 1-4 | 19 | 1-5 | 19 | 1-6 | 19 |
| 1-4 | 20 | 1-5 | 20 | 1-6 | 20 |
| 1-4 | 21 | 1-5 | 21 | 1-6 | 21 |
| 1-4 | 22 | 1-5 | 22 | 1-6 | 22 |
| 1-4 | 23 | 1-5 | 23 | 1-6 | 23 |
| 1-4 | 24 | 1-5 | 24 | 1-6 | 24 |
| 1-4 | 25 | 1-5 | 25 | 1-6 | 25 |
| 1-4 | 26 | 1-5 | 26 | 1-6 | 26 |
| 1-4 | 27 | 1-5 | 27 | 1-6 | 27 |
| 1-4 | 28 | 1-5 | 28 | 1-6 | 28 |
| 1-4 | 29 | 1-5 | 29 | 1-6 | 29 |
| 1-4 | 30 | 1-5 | 30 | 1-6 | 30 |
| 1-4 | 31 | 1-5 | 31 | 1-6 | 31 |
| 1-4 | 32 | 1-5 | 32 | 1-6 | 32 |
| 1-4 | 33 | 1-5 | 33 | 1-6 | 33 |
| 1-4 | 34 | 1-5 | 34 | 1-6 | 34 |
| 1-4 | 35 | 1-5 | 35 | 1-6 | 35 |
| 1-4 | 36 | 1-5 | 36 | 1-6 | 36 |
| 1-4 | 37 | 1-5 | 37 | 1-6 | 37 |
| 1-4 | 38 | 1-5 | 38 | 1-6 | 38 |
| 1-4 | 39 | 1-5 | 39 | 1-6 | 39 |
| 1-4 | 40 | 1-5 | 40 | 1-6 | 40 |
| 1-4 | 41 | 1-5 | 41 | 1-6 | 41 |
| 1-4 | 42 | 1-5 | 42 | 1-6 | 42 |
| 1-4 | 43 | 1-5 | 43 | 1-6 | 43 |
| 1-4 | 44 | 1-5 | 44 | 1-6 | 44 |
| 1-4 | 45 | 1-5 | 45 | 1-6 | 45 |
| 1-4 | 46 | 1-5 | 46 | 1-6 | 46 |
| 1-4 | 47 | 1-5 | 47 | 1-6 | 47 |
| 1-4 | 48 | 1-5 | 48 | 1-6 | 48 |
| 1-4 | 49 | 1-5 | 49 | 1-6 | 49 |
| 1-4 | 50 | 1-5 | 50 | 1-6 | 50 |
| 1-4 | 51 | 1-5 | 51 | 1-6 | 51 |
| 1-4 | 52 | 1-5 | 52 | 1-6 | 52 |
| 1-4 | 53 | 1-5 | 53 | 1-6 | 53 |
| 1-4 | 54 | 1-5 | 54 | 1-6 | 54 |
| 1-4 | 55 | 1-5 | 55 | 1-6 | 55 |
| 1-4 | 56 | 1-5 | 56 | 1-6 | 56 |
| 1-4 | 57 | 1-5 | 57 | 1-6 | 57 |
| 1-7 | 1 | 1-8 | 1 | 1-9 | 1 |
| 1-7 | 2 | 1-8 | 2 | 1-9 | 2 |
| 1-7 | 3 | 1-8 | 3 | 1-9 | 3 |
| 1-7 | 4 | 1-8 | 4 | 1-9 | 4 |
| 1-7 | 5 | 1-8 | 5 | 1-9 | 5 |
| 1-7 | 6 | 1-8 | 6 | 1-9 | 6 |
| 1-7 | 7 | 1-8 | 7 | 1-9 | 7 |
| 1-7 | 8 | 1-8 | 8 | 1-9 | 8 |
| 1-7 | 9 | 1-8 | 9 | 1-9 | 9 |
| 1-7 | 10 | 1-8 | 10 | 1-9 | 10 |
| 1-7 | 11 | 1-8 | 11 | 1-9 | 11 |
| 1-7 | 12 | 1-8 | 12 | 1-9 | 12 |
| 1-7 | 13 | 1-8 | 13 | 1-9 | 13 |
| 1-7 | 14 | 1-8 | 14 | 1-9 | 14 |
| 1-7 | 15 | 1-8 | 15 | 1-9 | 15 |
| 1-7 | 16 | 1-8 | 16 | 1-9 | 16 |
| 1-7 | 17 | 1-8 | 17 | 1-9 | 17 |
| 1-7 | 18 | 1-8 | 18 | 1-9 | 18 |
| 1-7 | 19 | 1-8 | 19 | 1-9 | 19 |
| 1-7 | 20 | 1-8 | 20 | 1-9 | 20 |
| 1-7 | 21 | 1-8 | 21 | 1-9 | 21 |
| 1-7 | 22 | 1-8 | 22 | 1-9 | 22 |
| 1-7 | 23 | 1-8 | 23 | 1-9 | 23 |
| 1-7 | 24 | 1-8 | 24 | 1-9 | 24 |
| 1-7 | 25 | 1-8 | 25 | 1-9 | 25 |
| 1-7 | 26 | 1-8 | 26 | 1-9 | 26 |
| 1-7 | 27 | 1-8 | 27 | 1-9 | 27 |
| 1-7 | 28 | 1-8 | 28 | 1-9 | 28 |
| 1-7 | 29 | 1-8 | 29 | 1-9 | 29 |
| 1-7 | 30 | 1-8 | 30 | 1-9 | 30 |
| 1-7 | 31 | 1-8 | 31 | 1-9 | 31 |
| 1-7 | 32 | 1-8 | 32 | 1-9 | 32 |
| 1-7 | 33 | 1-8 | 33 | 1-9 | 33 |
| 1-7 | 34 | 1-8 | 34 | 1-9 | 34 |
| 1-7 | 35 | 1-8 | 35 | 1-9 | 35 |
| 1-7 | 36 | 1-8 | 36 | 1-9 | 36 |
| 1-7 | 37 | 1-8 | 37 | 1-9 | 37 |
| 1-7 | 38 | 1-8 | 38 | 1-9 | 38 |
| 1-7 | 39 | 1-8 | 39 | 1-9 | 39 |
| 1-7 | 40 | 1-8 | 40 | 1-9 | 40 |
| 1-7 | 41 | 1-8 | 41 | 1-9 | 41 |
| 1-7 | 42 | 1-8 | 42 | 1-9 | 42 |
| 1-7 | 43 | 1-8 | 43 | 1-9 | 43 |
| 1-7 | 44 | 1-8 | 44 | 1-9 | 44 |
| 1-7 | 45 | 1-8 | 45 | 1-9 | 45 |
| 1-7 | 46 | 1-8 | 46 | 1-9 | 46 |
| 1-7 | 47 | 1-8 | 47 | 1-9 | 47 |
| 1-7 | 48 | 1-8 | 48 | 1-9 | 48 |
| 1-7 | 49 | 1-8 | 49 | 1-9 | 49 |
| 1-7 | 50 | 1-8 | 50 | 1-9 | 50 |
| 1-7 | 51 | 1-8 | 51 | 1-9 | 51 |
| 1-7 | 52 | 1-8 | 52 | 1-9 | 52 |
| 1-7 | 53 | 1-8 | 53 | 1-9 | 53 |
| 1-7 | 54 | 1-8 | 54 | 1-9 | 54 |
| 1-7 | 55 | 1-8 | 55 | 1-9 | 55 |
| 1-7 | 56 | 1-8 | 56 | 1-9 | 56 |
| 1-7 | 57 | 1-8 | 57 | 1-9 | 57 |
| 1-10 | 1 | 1-11 | 1 | 1-12 | 1 |
| 1-10 | 2 | 1-11 | 2 | 1-12 | 2 |
| 1-10 | 3 | 1-11 | 3 | 1-12 | 3 |
| 1-10 | 4 | 1-11 | 4 | 1-12 | 4 |
| 1-10 | 5 | 1-11 | 5 | 1-12 | 5 |
| 1-10 | 6 | 1-11 | 6 | 1-12 | 6 |
| 1-10 | 7 | 1-11 | 7 | 1-12 | 7 |
| 1-10 | 8 | 1-11 | 8 | 1-12 | 8 |
| 1-10 | 9 | 1-11 | 9 | 1-12 | 9 |
| 1-10 | 10 | 1-11 | 10 | 1-12 | 10 |
| 1-10 | 11 | 1-11 | 11 | 1-12 | 11 |
| 1-10 | 12 | 1-11 | 12 | 1-12 | 12 |
| 1-10 | 13 | 1-11 | 13 | 1-12 | 13 |
| 1-10 | 14 | 1-11 | 14 | 1-12 | 14 |
| 1-10 | 15 | 1-11 | 15 | 1-12 | 15 |
| 1-10 | 16 | 1-11 | 16 | 1-12 | 16 |
| 1-10 | 17 | 1-11 | 17 | 1-12 | 17 |
| 1-10 | 18 | 1-11 | 18 | 1-12 | 18 |
| 1-10 | 19 | 1-11 | 19 | 1-12 | 19 |
| 1-10 | 20 | 1-11 | 20 | 1-12 | 20 |
| 1-10 | 21 | 1-11 | 21 | 1-12 | 21 |
| 1-10 | 22 | 1-11 | 22 | 1-12 | 22 |

TABLE 2-continued

Sulfonylurea I' and II''
$A_{z-y}$—$SO_2$—NH—CO—NH—$P_n$ and
$A_{z-y}$—$SO_2$—NH—CO—NH—$T_n$

| $A_{x-y}$ | $P_n/T_n$ | $A_{x-y}$ | $P_n/T_n$ | $A_{x-y}$ | $P_n/T_n$ |
|---|---|---|---|---|---|
| 1-10 | 23 | 1-11 | 23 | 1-12 | 23 |
| 1-10 | 24 | 1-11 | 24 | 1-12 | 24 |
| 1-10 | 25 | 1-11 | 25 | 1-12 | 25 |
| 1-10 | 26 | 1-11 | 26 | 1-12 | 26 |
| 1-10 | 27 | 1-11 | 27 | 1-12 | 27 |
| 1-10 | 28 | 1-11 | 28 | 1-12 | 28 |
| 1-10 | 29 | 1-11 | 29 | 1-12 | 29 |
| 1-10 | 30 | 1-11 | 30 | 1-12 | 30 |
| 1-10 | 31 | 1-11 | 31 | 1-12 | 31 |
| 1-10 | 32 | 1-11 | 32 | 1-12 | 32 |
| 1-10 | 33 | 1-11 | 33 | 1-12 | 33 |
| 1-10 | 34 | 1-11 | 34 | 1-12 | 34 |
| 1-10 | 35 | 1-11 | 35 | 1-12 | 35 |
| 1-10 | 36 | 1-11 | 36 | 1-12 | 36 |
| 1-10 | 37 | 1-11 | 37 | 1-12 | 37 |
| 1-10 | 38 | 1-11 | 38 | 1-12 | 38 |
| 1-10 | 39 | 1-11 | 39 | 1-12 | 39 |
| 1-10 | 40 | 1-11 | 40 | 1-12 | 40 |
| 1-10 | 41 | 1-11 | 41 | 1-12 | 41 |
| 1-10 | 42 | 1-11 | 42 | 1-12 | 42 |
| 1-10 | 43 | 1-11 | 43 | 1-12 | 43 |
| 1-10 | 44 | 1-11 | 44 | 1-12 | 44 |
| 1-10 | 45 | 1-11 | 45 | 1-12 | 45 |
| 1-10 | 46 | 1-11 | 46 | 1-12 | 46 |
| 1-10 | 47 | 1-11 | 47 | 1-12 | 47 |
| 1-10 | 48 | 1-11 | 48 | 1-12 | 48 |
| 1-10 | 49 | 1-11 | 49 | 1-12 | 49 |
| 1-10 | 50 | 1-11 | 50 | 1-12 | 50 |
| 1-10 | 51 | 1-11 | 51 | 1-12 | 51 |
| 1-10 | 52 | 1-11 | 52 | 1-12 | 52 |
| 1-10 | 53 | 1-11 | 53 | 1-12 | 53 |
| 1-10 | 54 | 1-11 | 54 | 1-12 | 54 |
| 1-10 | 55 | 1-11 | 55 | 1-12 | 55 |
| 1-10 | 56 | 1-11 | 56 | 1-12 | 56 |
| 1-10 | 57 | 1-11 | 57 | 1-12 | 57 |
| 1-13 | 1 | | | | |
| 1-13 | 2 | | | | |
| 1-13 | 3 | | | | |
| 1-13 | 4 | | | | |
| 1-13 | 5 | | | | |
| 1-13 | 6 | | | | |
| 1-13 | 7 | | | | |
| 1-13 | 8 | | | | |
| 1-13 | 9 | 1-13 | 50 | | |
| 1-13 | 10 | 1-13 | 51 | | |
| 1-13 | 11 | 1-13 | 52 | | |
| 1-13 | 12 | 1-13 | 53 | | |
| 1-13 | 13 | 1-13 | 54 | | |
| 1-13 | 14 | 1-13 | 55 | | |
| 1-13 | 15 | 1-13 | 56 | | |
| 1-13 | 16 | 1-13 | 57 | | |
| 1-13 | 17 | | | | |
| 1-13 | 18 | | | | |
| 1-13 | 19 | | | | |
| 1-13 | 20 | | | | |
| 1-13 | 21 | | | | |
| 1-13 | 22 | | | | |
| 1-13 | 23 | | | | |
| 1-13 | 24 | | | | |
| 1-13 | 25 | | | | |
| 1-13 | 26 | | | | |
| 1-13 | 27 | | | | |
| 1-13 | 28 | | | | |
| 1-13 | 29 | | | | |
| 1-13 | 30 | | | | |
| 1-13 | 31 | | | | |
| 1-13 | 32 | | | | |
| 1-13 | 33 | | | | |
| 1-13 | 34 | | | | |
| 1-13 | 35 | | | | |
| 1-13 | 36 | | | | |
| 1-13 | 37 | | | | |
| 1-13 | 38 | | | | |
| 1-13 | 39 | | | | |
| 1-13 | 40 | | | | |
| 1-13 | 41 | | | | |
| 1-13 | 42 | | | | |
| 1-13 | 43 | | | | |
| 1-13 | 44 | | | | |
| 1-13 | 45 | | | | |
| 1-13 | 46 | | | | |
| 1-13 | 47 | | | | |
| 1-13 | 48 | | | | |
| 1-13 | 49 | | | | |
| 2-1 | 1 | 2-2 | 1 | 2-3 | 1 |
| 2-1 | 2 | 2-2 | 2 | 2-3 | 2 |
| 2-1 | 3 | 2-2 | 3 | 2-3 | 3 |
| 2-1 | 4 | 2-2 | 4 | 2-3 | 4 |
| 2-1 | 5 | 2-2 | 5 | 2-3 | 5 |
| 2-1 | 6 | 2-2 | 6 | 2-3 | 6 |
| 2-1 | 7 | 2-2 | 7 | 2-3 | 7 |
| 2-1 | 8 | 2-2 | 8 | 2-3 | 8 |
| 2-1 | 9 | 2-2 | 9 | 2-3 | 9 |
| 2-1 | 10 | 2-2 | 10 | 2-3 | 10 |
| 2-1 | 11 | 2-2 | 11 | 2-3 | 11 |
| 2-1 | 12 | 2-2 | 12 | 2-3 | 12 |
| 2-1 | 13 | 2-2 | 13 | 2-3 | 13 |
| 2-1 | 14 | 2-2 | 11 | 2-3 | 14 |
| 2-1 | 15 | 2-2 | 15 | 2-3 | 15 |
| 2-1 | 16 | 2-2 | 16 | 2-3 | 16 |
| 2-1 | 17 | 2-2 | 17 | 2-3 | 17 |
| 2-1 | 18 | 2-2 | 18 | 2-3 | 18 |
| 2-1 | 19 | 2-2 | 19 | 2-3 | 19 |
| 2-1 | 20 | 2-2 | 20 | 2-3 | 20 |
| 2-1 | 21 | 2-2 | 21 | 2-3 | 21 |
| 2-1 | 22 | 2-2 | 22 | 2-3 | 22 |
| 2-1 | 23 | 2-2 | 23 | 2-3 | 23 |
| 2-1 | 24 | 2-2 | 24 | 2-3 | 24 |
| 2-1 | 25 | 2-2 | 25 | 2-3 | 25 |
| 2-1 | 26 | 2-2 | 26 | 2-3 | 26 |
| 2-1 | 27 | 2-2 | 27 | 2-3 | 27 |
| 2-1 | 28 | 2-2 | 28 | 2-3 | 28 |
| 2-1 | 29 | 2-2 | 29 | 2-3 | 29 |
| 2-1 | 30 | 2-2 | 30 | 2-3 | 30 |
| 2-1 | 31 | 2-2 | 31 | 2-3 | 31 |
| 2-1 | 32 | 2-2 | 32 | 2-3 | 32 |
| 2-1 | 33 | 2-2 | 33 | 2-3 | 33 |
| 2-1 | 34 | 2-2 | 34 | 2-3 | 34 |
| 2-1 | 35 | 2-2 | 35 | 2-3 | 35 |
| 2-1 | 36 | 2-2 | 36 | 2-3 | 36 |
| 2-1 | 37 | 2-2 | 37 | 2-3 | 37 |
| 2-1 | 38 | 2-2 | 38 | 2-3 | 38 |
| 2-1 | 39 | 2-2 | 39 | 2-3 | 39 |
| 2-1 | 40 | 2-2 | 40 | 2-3 | 40 |
| 2-1 | 41 | 2-2 | 41 | 2-3 | 41 |
| 2-1 | 42 | 2-2 | 42 | 2-3 | 42 |
| 2-1 | 43 | 2-2 | 43 | 2-3 | 43 |
| 2-1 | 44 | 2-2 | 44 | 2-3 | 44 |
| 2-1 | 45 | 2-2 | 45 | 2-3 | 45 |
| 2-1 | 46 | 2-2 | 46 | 2-3 | 46 |
| 2-1 | 47 | 2-2 | 47 | 2-3 | 47 |
| 2-1 | 48 | 2-2 | 48 | 2-3 | 48 |
| 2-1 | 49 | 2-2 | 49 | 2-3 | 49 |
| 2-1 | 50 | 2-2 | 50 | 2-3 | 50 |
| 2-1 | 51 | 2-2 | 51 | 2-3 | 51 |
| 2-1 | 52 | 2-2 | 52 | 2-3 | 52 |
| 2-1 | 53 | 2-2 | 53 | 2-3 | 53 |
| 2-1 | 54 | 2-2 | 54 | 2-3 | 54 |
| 2-1 | 55 | 2-2 | 55 | 2-3 | 55 |
| 2-1 | 56 | 2-2 | 56 | 2-3 | 56 |
| 2-1 | 57 | 2-2 | 57 | 2-3 | 57 |
| 2-4 | 1 | 2-5 | 1 | 2-6 | 1 |
| 2-4 | 2 | 2-5 | 2 | 2-6 | 2 |
| 2-4 | 3 | 2-5 | 3 | 2-6 | 3 |
| 2-4 | 4 | 2-5 | 4 | 2-6 | 4 |
| 2-4 | 5 | 2-5 | 5 | 2-6 | 5 |
| 2-4 | 6 | 2-5 | 6 | 2-6 | 6 |
| 2-4 | 7 | 2-5 | 7 | 2-6 | 7 |
| 2-4 | 8 | 2-5 | 8 | 2-6 | 8 |
| 2-4 | 9 | 2-5 | 9 | 2-6 | 9 |
| 2-4 | 10 | 2-5 | 10 | 2-6 | 10 |
| 2-4 | 11 | 2-5 | 11 | 2-6 | 11 |
| 2-4 | 12 | 2-5 | 12 | 2-6 | 12 |
| 2-4 | 13 | 2-5 | 13 | 2-6 | 13 |

TABLE 2-continued

Sulfonylurea I' and II''
$A_{z-y}$—$SO_2$—NH—CO—NH—$P_n$ and
$A_{z-y}$—$SO_2$—NH—CO—NH—$T_n$

| $A_{x-y}$ | $P_n/T_n$ | $A_{x-y}$ | $P_n/T_n$ | $A_{x-y}$ | $P_n/T_n$ |
|---|---|---|---|---|---|
| 2-4 | 14 | 2-5 | 14 | 2-6 | 14 |
| 2-4 | 15 | 2-5 | 15 | 2-6 | 15 |
| 2-4 | 16 | 2-5 | 16 | 2-6 | 16 |
| 2-4 | 17 | 2-5 | 17 | 2-6 | 17 |
| 2-4 | 18 | 2-5 | 18 | 2-6 | 18 |
| 2-4 | 19 | 2-5 | 19 | 2-6 | 19 |
| 2-4 | 20 | 2-5 | 20 | 2-6 | 20 |
| 2-4 | 21 | 2-5 | 21 | 2-6 | 21 |
| 2-4 | 22 | 2-5 | 22 | 2-6 | 22 |
| 2-4 | 23 | 2-5 | 23 | 2-6 | 23 |
| 2-4 | 24 | 2-5 | 24 | 2-6 | 24 |
| 2-4 | 25 | 2-5 | 25 | 2-6 | 25 |
| 2-4 | 26 | 2-5 | 26 | 2-6 | 26 |
| 2-4 | 27 | 2-5 | 27 | 2-6 | 27 |
| 2-4 | 28 | 2-5 | 28 | 2-6 | 28 |
| 2-4 | 29 | 2-5 | 29 | 2-6 | 29 |
| 2-4 | 30 | 2-5 | 30 | 2-6 | 30 |
| 2-4 | 31 | 2-5 | 31 | 2-6 | 31 |
| 2-4 | 32 | 2-5 | 32 | 2-6 | 32 |
| 2-4 | 33 | 2-5 | 33 | 2-6 | 33 |
| 2-4 | 34 | 2-5 | 34 | 2-6 | 34 |
| 2-4 | 35 | 2-5 | 35 | 2-6 | 35 |
| 2-4 | 36 | 2-5 | 36 | 2-6 | 36 |
| 2-4 | 37 | 2-5 | 37 | 2-6 | 37 |
| 2-4 | 38 | 2-5 | 38 | 2-6 | 38 |
| 2-4 | 39 | 2-5 | 39 | 2-6 | 39 |
| 2-4 | 40 | 2-5 | 40 | 2-6 | 40 |
| 2-4 | 41 | 2-5 | 41 | 2-6 | 41 |
| 2-4 | 42 | 2-5 | 42 | 2-6 | 42 |
| 2-4 | 43 | 2-5 | 43 | 2-6 | 43 |
| 2-4 | 44 | 2-5 | 44 | 2-6 | 44 |
| 2-4 | 45 | 2-5 | 45 | 2-6 | 45 |
| 2-4 | 46 | 2-5 | 46 | 2-6 | 46 |
| 2-4 | 47 | 2-5 | 47 | 2-6 | 47 |
| 2-4 | 48 | 2-5 | 48 | 2-6 | 48 |
| 2-4 | 49 | 2-5 | 49 | 2-6 | 49 |
| 2-4 | 50 | 2-5 | 50 | 2-6 | 50 |
| 2-4 | 51 | 2-5 | 51 | 2-6 | 51 |
| 2-4 | 52 | 2-5 | 52 | 2-6 | 52 |
| 2-4 | 53 | 2-5 | 53 | 2-6 | 53 |
| 2-4 | 54 | 2-5 | 54 | 2-6 | 54 |
| 2-4 | 55 | 2-5 | 55 | 2-6 | 55 |
| 2-4 | 56 | 2-5 | 56 | 2-6 | 56 |
| 2-4 | 57 | 2-5 | 57 | 2-6 | 57 |
| 2-7 | 1 | 2-8 | 1 | 2-9 | 1 |
| 2-7 | 2 | 2-8 | 2 | 2-9 | 2 |
| 2-7 | 3 | 2-8 | 3 | 2-9 | 3 |
| 2-7 | 4 | 2-8 | 4 | 2-9 | 4 |
| 2-7 | 5 | 2-8 | 5 | 2-9 | 5 |
| 2-7 | 6 | 2-8 | 6 | 2-9 | 6 |
| 2-7 | 7 | 2-8 | 7 | 2-9 | 7 |
| 2-7 | 8 | 2-8 | 8 | 2-9 | 8 |
| 2-7 | 9 | 2-8 | 9 | 2-9 | 9 |
| 2-7 | 10 | 2-8 | 10 | 2-9 | 10 |
| 2-7 | 11 | 2-8 | 11 | 2-9 | 11 |
| 2-7 | 12 | 2-8 | 12 | 2-9 | 12 |
| 2-7 | 13 | 2-8 | 13 | 2-9 | 13 |
| 2-7 | 14 | 2-8 | 14 | 2-9 | 14 |
| 2-7 | 15 | 2-8 | 15 | 2-9 | 15 |
| 2-7 | 16 | 2-8 | 16 | 2-9 | 16 |
| 2-7 | 17 | 2-8 | 17 | 2-9 | 17 |
| 2-7 | 18 | 2-8 | 18 | 2-9 | 18 |
| 2-7 | 19 | 2-8 | 19 | 2-9 | 19 |
| 2-7 | 20 | 2-8 | 20 | 2-9 | 20 |
| 2-7 | 21 | 2-8 | 21 | 2-9 | 21 |
| 2-7 | 22 | 2-8 | 22 | 2-9 | 22 |
| 2-7 | 23 | 2-8 | 23 | 2-9 | 23 |
| 2-7 | 24 | 2-8 | 24 | 2-9 | 24 |
| 2-7 | 25 | 2-8 | 25 | 2-9 | 25 |
| 2-7 | 26 | 2-8 | 26 | 2-9 | 26 |
| 2-7 | 27 | 2-8 | 27 | 2-9 | 27 |
| 2-7 | 28 | 2-8 | 28 | 2-9 | 28 |
| 2-7 | 29 | 2-8 | 29 | 2-9 | 29 |
| 2-7 | 30 | 2-8 | 30 | 2-9 | 30 |
| 2-7 | 31 | 2-8 | 31 | 2-9 | 31 |
| 2-7 | 32 | 2-8 | 32 | 2-9 | 32 |
| 2-7 | 33 | 2-8 | 33 | 2-9 | 33 |
| 2-7 | 34 | 2-8 | 34 | 2-9 | 34 |
| 2-7 | 35 | 2-8 | 35 | 2-9 | 35 |
| 2-7 | 36 | 2-8 | 36 | 2-9 | 36 |
| 2-7 | 37 | 2-8 | 37 | 2-9 | 37 |
| 2-7 | 38 | 2-8 | 38 | 2-9 | 38 |
| 2-7 | 39 | 2-8 | 39 | 2-9 | 39 |
| 2-7 | 40 | 2-8 | 40 | 2-9 | 40 |
| 2-7 | 41 | 2-8 | 41 | 2-9 | 41 |
| 2-7 | 42 | 2-8 | 42 | 2-9 | 42 |
| 2-7 | 43 | 2-8 | 43 | 2-9 | 43 |
| 2-7 | 44 | 2-8 | 44 | 2-9 | 44 |
| 2-7 | 45 | 2-8 | 45 | 2-9 | 45 |
| 2-7 | 46 | 2-8 | 46 | 2-9 | 46 |
| 2-7 | 47 | 2-8 | 47 | 2-9 | 47 |
| 2-7 | 48 | 2-8 | 48 | 2-9 | 48 |
| 2-7 | 49 | 2-8 | 49 | 2-9 | 49 |
| 2-7 | 50 | 2-8 | 50 | 2-9 | 50 |
| 2-7 | 51 | 2-8 | 51 | 2-9 | 51 |
| 2-7 | 52 | 2-8 | 52 | 2-9 | 52 |
| 2-7 | 53 | 2-8 | 53 | 2-9 | 53 |
| 2-7 | 54 | 2-8 | 54 | 2-9 | 54 |
| 2-7 | 55 | 2-8 | 55 | 2-9 | 55 |
| 2-7 | 56 | 2-8 | 56 | 2-9 | 56 |
| 2-7 | 57 | 2-8 | 57 | 2-9 | 57 |
| 2-10 | 1 | 2-11 | 1 | 2-12 | 1 |
| 2-10 | 2 | 2-11 | 2 | 2-12 | 2 |
| 2-10 | 3 | 2-11 | 3 | 2-12 | 3 |
| 2-10 | 4 | 2-11 | 4 | 2-12 | 4 |
| 2-10 | 5 | 2-11 | 5 | 2-12 | 5 |
| 2-10 | 6 | 2-11 | 6 | 2-12 | 6 |
| 2-10 | 7 | 2-11 | 7 | 2-12 | 7 |
| 2-10 | 8 | 2-11 | 8 | 2-12 | 8 |
| 2-10 | 9 | 2-11 | 9 | 2-12 | 9 |
| 2-10 | 10 | 2-11 | 10 | 2-12 | 10 |
| 2-10 | 11 | 2-11 | 11 | 2-12 | 11 |
| 2-10 | 12 | 2-11 | 12 | 2-12 | 12 |
| 2-10 | 13 | 2-11 | 13 | 2-12 | 13 |
| 2-10 | 14 | 2-11 | 14 | 2-12 | 14 |
| 2-10 | 15 | 2-11 | 15 | 2-12 | 15 |
| 2-10 | 16 | 2-11 | 16 | 2-12 | 16 |
| 2-10 | 17 | 2-11 | 17 | 2-12 | 17 |
| 2-10 | 17 | 2-11 | 17 | 2-12 | 17 |
| 2-10 | 18 | 2-11 | 18 | 2-12 | 18 |
| 2-10 | 19 | 2-11 | 19 | 2-12 | 19 |
| 2-10 | 20 | 2-11 | 20 | 2-12 | 20 |
| 2-10 | 21 | 2-11 | 21 | 2-12 | 21 |
| 2-10 | 22 | 2-11 | 22 | 2-12 | 22 |
| 2-10 | 23 | 2-11 | 23 | 2-12 | 23 |
| 2-10 | 24 | 2-11 | 24 | 2-12 | 24 |
| 2-10 | 25 | 2-11 | 25 | 2-12 | 25 |
| 2-10 | 26 | 2-11 | 26 | 2-12 | 26 |
| 2-10 | 27 | 2-11 | 27 | 2-12 | 27 |
| 2-10 | 28 | 2-11 | 28 | 2-12 | 28 |
| 2-10 | 29 | 2-11 | 29 | 2-12 | 29 |
| 2-10 | 30 | 2-11 | 30 | 2-12 | 30 |
| 2-10 | 31 | 2-11 | 31 | 2-12 | 31 |
| 2-10 | 32 | 2-11 | 32 | 2-12 | 32 |
| 2-10 | 33 | 2-11 | 33 | 2-12 | 33 |
| 2-10 | 34 | 2-11 | 34 | 2-12 | 34 |
| 2-10 | 35 | 2-11 | 35 | 2-12 | 35 |
| 2-10 | 36 | 2-11 | 36 | 2-12 | 36 |
| 2-10 | 37 | 2-11 | 37 | 2-12 | 37 |
| 2-10 | 38 | 2-11 | 38 | 2-12 | 38 |
| 2-10 | 39 | 2-11 | 39 | 2-12 | 39 |
| 2-10 | 40 | 2-11 | 40 | 2-12 | 40 |
| 2-10 | 41 | 2-11 | 41 | 2-12 | 41 |
| 2-10 | 42 | 2-11 | 42 | 2-12 | 42 |
| 2-10 | 43 | 2-11 | 43 | 2-12 | 43 |
| 2-10 | 44 | 2-11 | 44 | 2-12 | 44 |
| 2-10 | 45 | 2-11 | 45 | 2-12 | 45 |
| 2-10 | 46 | 2-11 | 46 | 2-12 | 46 |
| 2-10 | 47 | 2-11 | 47 | 2-12 | 47 |
| 2-10 | 48 | 2-11 | 48 | 2-12 | 48 |
| 2-10 | 49 | 2-11 | 49 | 2-12 | 49 |
| 2-10 | 50 | 2-11 | 50 | 2-12 | 50 |
| 2-10 | 51 | 2-11 | 51 | 2-12 | 51 |
| 2-10 | 52 | 2-11 | 52 | 2-12 | 52 |

TABLE 2-continued

Sulfonylurea I' and II''
$A_{z-y}$—SO$_2$—NH—CO—NH—P$_n$ and
$A_{z-y}$—SO$_2$—NH—CO—NH—T$_n$

| $A_{x-y}$ | P$_n$/T$_n$ | $A_{x-y}$ | P$_n$/T$_n$ | $A_{x-y}$ | P$_n$/T$_n$ |
|---|---|---|---|---|---|
| 2-10 | 53 | 2-11 | 53 | 2-12 | 53 |
| 2-10 | 54 | 2-11 | 54 | 2-12 | 54 |
| 2-10 | 55 | 2-11 | 55 | 2-12 | 55 |
| 2-10 | 56 | 2-11 | 56 | 2-12 | 56 |
| 2-10 | 57 | 2-11 | 57 | 2-12 | 57 |
| 2-13 | 1 | 2-13 | 42 | | |
| 2-13 | 2 | 2-13 | 43 | | |
| 2-13 | 3 | 2-13 | 44 | | |
| 2-13 | 4 | 2-13 | 45 | | |
| 2-13 | 5 | 2-13 | 46 | | |
| 2-13 | 6 | 2-13 | 47 | | |
| 2-13 | 7 | 2-13 | 48 | | |
| 2-13 | 8 | 2-13 | 49 | | |
| 2-13 | 9 | 2-13 | 50 | | |
| 2-13 | 10 | 2-13 | 51 | | |
| 2-13 | 11 | 2-13 | 52 | | |
| 2-13 | 12 | 2-13 | 53 | | |
| 2-13 | 13 | 2-13 | 54 | | |
| 2-13 | 14 | 2-13 | 55 | | |
| 2-13 | 15 | 2-13 | 56 | | |
| 2-13 | 16 | 2-13 | 56 | | |
| 2-13 | 17 | 2-13 | 57 | | |
| 2-13 | 18 | | | | |
| 2-13 | 19 | | | | |
| 2-13 | 20 | | | | |
| 2-13 | 21 | | | | |
| 2-13 | 22 | | | | |
| 2-13 | 23 | | | | |
| 2-13 | 24 | | | | |
| 2-13 | 25 | | | | |
| 2-13 | 26 | | | | |
| 2-13 | 27 | | | | |
| 2-13 | 28 | | | | |
| 2-13 | 29 | | | | |
| 2-13 | 30 | | | | |
| 2-13 | 31 | | | | |
| 2-13 | 32 | | | | |
| 2-13 | 33 | | | | |
| 2-13 | 34 | | | | |
| 2-13 | 35 | | | | |
| 2-13 | 36 | | | | |
| 2-13 | 37 | | | | |
| 2-13 | 38 | | | | |
| 2-13 | 39 | | | | |
| 2-13 | 40 | | | | |
| 2-13 | 41 | | | | |
| 3-1 | 1 | 4-1 | 1 | 5-1 | 1 |
| 3-1 | 2 | 4-1 | 2 | 5-1 | 2 |
| 3-1 | 3 | 4-1 | 3 | 5-1 | 3 |
| 3-1 | 4 | 4-1 | 4 | 5-1 | 4 |
| 3-1 | 5 | 4-1 | 5 | 5-1 | 5 |
| 3-1 | 6 | 4-1 | 6 | 5-1 | 6 |
| 3-1 | 7 | 4-1 | 7 | 5-1 | 7 |
| 3-1 | 8 | 4-1 | 8 | 5-1 | 8 |
| 3-1 | 9 | 4-1 | 9 | 5-1 | 9 |
| 3-1 | 10 | 4-1 | 10 | 5-1 | 10 |
| 3-1 | 11 | 4-1 | 11 | 5-1 | 11 |
| 3-1 | 12 | 4-1 | 12 | 5-1 | 12 |
| 3-1 | 13 | 4-1 | 13 | 5-1 | 13 |
| 3-1 | 14 | 4-1 | 14 | 5-1 | 14 |
| 3-1 | 15 | 4-1 | 15 | 5-1 | 15 |
| 3-1 | 16 | 4-1 | 16 | 5-1 | 16 |
| 3-1 | 17 | 4-1 | 17 | 5-1 | 17 |
| 3-1 | 18 | 4-1 | 18 | 5-1 | 18 |
| 3-1 | 19 | 4-1 | 19 | 5-1 | 19 |
| 3-1 | 20 | 4-1 | 20 | 5-1 | 20 |
| 3-1 | 21 | 4-1 | 21 | 5-1 | 21 |
| 3-1 | 22 | 4-1 | 22 | 5-1 | 22 |
| 3-1 | 23 | 4-1 | 23 | 5-1 | 23 |
| 3-1 | 24 | 4-1 | 24 | 5-1 | 24 |
| 3-1 | 25 | 4-1 | 25 | 5-1 | 25 |
| 3-1 | 26 | 4-1 | 26 | 5-1 | 26 |
| 3-1 | 27 | 4-1 | 27 | 5-1 | 27 |
| 3-1 | 28 | 4-1 | 28 | 5-1 | 28 |
| 3-1 | 29 | 4-1 | 29 | 5-1 | 29 |
| 3-1 | 30 | 4-1 | 30 | 5-1 | 30 |
| 3-1 | 31 | 4-1 | 31 | 5-1 | 31 |
| 3-1 | 32 | 4-1 | 32 | 5-1 | 32 |
| 3-1 | 33 | 4-1 | 33 | 5-1 | 33 |
| 3-1 | 34 | 4-1 | 34 | 5-1 | 34 |
| 3-1 | 35 | 4-1 | 35 | 5-1 | 35 |
| 3-1 | 36 | 4-1 | 36 | 5-1 | 36 |
| 3-1 | 37 | 4-1 | 37 | 5-1 | 37 |
| 3-1 | 38 | 4-1 | 38 | 5-1 | 38 |
| 3-1 | 39 | 4-1 | 39 | 5-1 | 39 |
| 3-1 | 40 | 4-1 | 40 | 5-1 | 40 |
| 3-1 | 41 | 4-1 | 41 | 5-1 | 41 |
| 3-1 | 42 | 4-1 | 42 | 5-1 | 42 |
| 3-1 | 43 | 4-1 | 43 | 5-1 | 43 |
| 3-1 | 44 | 4-1 | 44 | 5-1 | 44 |
| 3-1 | 45 | 4-1 | 45 | 5-1 | 45 |
| 3-1 | 46 | 4-1 | 46 | 5-1 | 46 |
| 3-1 | 47 | 4-1 | 47 | 5-1 | 47 |
| 3-1 | 48 | 4-1 | 48 | 5-1 | 48 |
| 3-1 | 49 | 4-1 | 49 | 5-1 | 49 |
| 3-1 | 50 | 4-1 | 50 | 5-1 | 50 |
| 3-1 | 51 | 4-1 | 51 | 5-1 | 51 |
| 3-1 | 52 | 4-1 | 52 | 5-1 | 52 |
| 3-1 | 53 | 4-1 | 53 | 5-1 | 53 |
| 3-1 | 54 | 4-1 | 54 | 5-1 | 54 |
| 3-1 | 55 | 4-1 | 55 | 5-1 | 55 |
| 3-1 | 56 | 4-1 | 56 | 5-1 | 56 |
| 3-1 | 57 | 4-1 | 57 | 5-1 | 57 |
| 6-1 | 1 | 7-1 | 1 | 8-1 | 1 |
| 6-1 | 2 | 7-1 | 2 | 8-1 | 2 |
| 6-1 | 3 | 7-1 | 3 | 8-1 | 3 |
| 6-1 | 4 | 7-1 | 4 | 8-1 | 4 |
| 6-1 | 5 | 7-1 | 5 | 8-1 | 5 |
| 6-1 | 6 | 7-1 | 6 | 8-1 | 6 |
| 6-1 | 7 | 7-1 | 7 | 8-1 | 7 |
| 6-1 | 8 | 7-1 | 8 | 8-1 | 8 |
| 6-1 | 9 | 7-1 | 9 | 8-1 | 9 |
| 6-1 | 10 | 7-1 | 10 | 8-1 | 10 |
| 6-1 | 11 | 7-1 | 11 | 8-1 | 11 |
| 6-1 | 12 | 7-1 | 12 | 8-1 | 12 |
| 6-1 | 13 | 7-1 | 13 | 8-1 | 13 |
| 6-1 | 14 | 7-1 | 14 | 8-1 | 14 |
| 6-1 | 15 | 7-1 | 15 | 8-1 | 15 |
| 6-1 | 16 | 7-1 | 16 | 8-1 | 16 |
| 6-1 | 17 | 7-1 | 17 | 8-1 | 17 |
| 6-1 | 18 | 7-1 | 18 | 8-1 | 18 |
| 6-1 | 19 | 7-1 | 19 | 8-1 | 19 |
| 6-1 | 20 | 7-1 | 20 | 8-1 | 20 |
| 6-1 | 21 | 7-1 | 21 | 8-1 | 21 |
| 6-1 | 22 | 7-1 | 22 | 8-1 | 22 |
| 6-1 | 23 | 7-1 | 23 | 8-1 | 23 |
| 6-1 | 24 | 7-1 | 24 | 8-1 | 24 |
| 6-1 | 25 | 7-1 | 25 | 8-1 | 25 |
| 6-1 | 26 | 7-1 | 26 | 8-1 | 26 |
| 6-1 | 27 | 7-1 | 27 | 8-1 | 27 |
| 6-1 | 28 | 7-1 | 28 | 8-1 | 28 |
| 6-1 | 29 | 7-1 | 29 | 8-1 | 29 |
| 6-1 | 30 | 7-1 | 30 | 8-1 | 30 |
| 6-1 | 31 | 7-1 | 31 | 8-1 | 31 |
| 6-1 | 32 | 7-1 | 32 | 8-1 | 32 |
| 6-1 | 33 | 7-1 | 33 | 8-1 | 33 |
| 6-1 | 34 | 7-1 | 34 | 8-1 | 34 |
| 6-1 | 35 | 7-1 | 35 | 8-1 | 35 |
| 6-1 | 36 | 7-1 | 36 | 8-1 | 36 |
| 6-1 | 37 | 7-1 | 37 | 8-1 | 37 |
| 6-1 | 38 | 7-1 | 38 | 8-1 | 38 |
| 6-1 | 39 | 7-1 | 39 | 8-1 | 39 |
| 6-1 | 40 | 7-1 | 40 | 8-1 | 40 |
| 6-1 | 41 | 7-1 | 41 | 8-1 | 41 |
| 6-1 | 42 | 7-1 | 42 | 8-1 | 42 |
| 6-1 | 43 | 7-1 | 43 | 8-1 | 43 |
| 6-1 | 44 | 7-1 | 44 | 8-1 | 44 |
| 6-1 | 45 | 7-1 | 45 | 8-1 | 45 |
| 6-1 | 46 | 7-1 | 46 | 8-1 | 46 |
| 6-1 | 47 | 7-1 | 47 | 8-1 | 47 |
| 6-1 | 48 | 7-1 | 48 | 8-1 | 48 |
| 6-1 | 49 | 7-1 | 49 | 8-1 | 49 |
| 6-1 | 50 | 7-1 | 50 | 8-1 | 50 |
| 6-1 | 51 | 7-1 | 51 | 8-1 | 51 |

TABLE 2-continued

Sulfonylurea I' and II''
$A_{z-y}$—SO$_2$—NH—CO—NH—P$_n$ and
$A_{z-y}$—SO$_2$—NH—CO—NH—T$_n$

| $A_{x-y}$ | P$_n$/T$_n$ | $A_{x-y}$ | P$_n$/T$_n$ | $A_{x-y}$ | P$_n$/T$_n$ |
|---|---|---|---|---|---|
| 6-1 | 52 | 7-1 | 52 | 8-1 | 52 |
| 6-1 | 53 | 7-1 | 53 | 8-1 | 53 |
| 6-1 | 54 | 7-1 | 54 | 8-1 | 54 |
| 6-1 | 55 | 7-1 | 55 | 8-1 | 55 |
| 6-1 | 56 | 7-1 | 56 | 8-1 | 56 |
| 6-1 | 57 | 7-1 | 57 | 8-1 | 57 |
| 9-1 | 1 | 10-1 | 1 | 11-1 | 1 |
| 9-1 | 2 | 10-1 | 2 | 11-1 | 2 |
| 9-1 | 3 | 10-1 | 3 | 11-1 | 3 |
| 9-1 | 4 | 10-1 | 4 | 11-1 | 4 |
| 9-1 | 5 | 10-1 | 5 | 11-1 | 5 |
| 9-1 | 6 | 10-1 | 6 | 11-1 | 6 |
| 9-1 | 7 | 10-1 | 7 | 11-1 | 7 |
| 9-1 | 8 | 10-1 | 8 | 11-1 | 8 |
| 9-1 | 9 | 10-1 | 9 | 11-1 | 9 |
| 9-1 | 10 | 10-1 | 10 | 11-1 | 10 |
| 9-1 | 11 | 10-1 | 11 | 11-1 | 11 |
| 9-1 | 12 | 10-1 | 12 | 11-1 | 12 |
| 9-1 | 13 | 10-1 | 13 | 11-1 | 13 |
| 9-1 | 14 | 10-1 | 14 | 11-1 | 14 |
| 9-1 | 15 | 10-1 | 15 | 11-1 | 15 |
| 9-1 | 16 | 10-1 | 16 | 11-1 | 16 |
| 9-1 | 17 | 10-1 | 17 | 11-1 | 17 |
| 9-1 | 18 | 10-1 | 18 | 11-1 | 18 |
| 9-1 | 19 | 10-1 | 19 | 11-1 | 19 |
| 9-1 | 20 | 10-1 | 20 | 11-1 | 20 |
| 9-1 | 21 | 10-1 | 21 | 11-1 | 21 |
| 9-1 | 22 | 10-1 | 22 | 11-1 | 22 |
| 9-1 | 23 | 10-1 | 23 | 11-1 | 23 |
| 9-1 | 24 | 10-1 | 24 | 11-1 | 24 |
| 9-1 | 25 | 10-1 | 25 | 11-1 | 25 |
| 9-1 | 26 | 10-1 | 26 | 11-1 | 26 |
| 9-1 | 27 | 10-1 | 27 | 11-1 | 27 |
| 9-1 | 27 | 10-1 | 27 | 11-1 | 27 |
| 9-1 | 28 | 10-1 | 28 | 11-1 | 28 |
| 9-1 | 29 | 10-1 | 29 | 11-1 | 29 |
| 9-1 | 30 | 10-1 | 30 | 11-1 | 30 |
| 9-1 | 31 | 10-1 | 31 | 11-1 | 31 |
| 9-1 | 32 | 10-1 | 32 | 11-1 | 32 |
| 9-1 | 33 | 10-1 | 33 | 11-1 | 33 |
| 9-1 | 34 | 10-1 | 34 | 11-1 | 34 |
| 9-1 | 35 | 10-1 | 35 | 11-1 | 35 |
| 9-1 | 36 | 10-1 | 36 | 11-1 | 36 |
| 9-1 | 37 | 10-1 | 37 | 11-1 | 37 |
| 9-1 | 38 | 10-1 | 38 | 11-1 | 38 |
| 9-1 | 39 | 10-1 | 39 | 11-1 | 39 |
| 9-1 | 40 | 10-1 | 40 | 11-1 | 40 |
| 9-1 | 41 | 10-1 | 41 | 11-1 | 41 |
| 9-1 | 42 | 10-1 | 42 | 11-1 | 42 |
| 9-1 | 43 | 10-1 | 43 | 11-1 | 43 |
| 9-1 | 44 | 10-1 | 44 | 11-1 | 44 |
| 9-1 | 45 | 10-1 | 45 | 11-1 | 45 |
| 9-1 | 46 | 10-1 | 46 | 11-1 | 46 |
| 9-1 | 47 | 10-1 | 47 | 11-1 | 47 |
| 9-1 | 48 | 10-1 | 48 | 11-1 | 48 |
| 9-1 | 49 | 10-1 | 49 | 11-1 | 49 |
| 9-1 | 50 | 10-1 | 50 | 11-1 | 50 |
| 9-1 | 51 | 10-1 | 51 | 11-1 | 51 |
| 9-1 | 52 | 10-1 | 52 | 11-1 | 52 |
| 9-1 | 53 | 10-1 | 53 | 11-1 | 53 |
| 9-1 | 54 | 10-1 | 54 | 11-1 | 54 |
| 9-1 | 55 | 10-1 | 55 | 11-1 | 55 |
| 9-1 | 56 | 10-1 | 56 | 11-1 | 56 |
| 9-1 | 57 | 10-1 | 57 | 11-1 | 57 |
| 12-1 | 1 | 13-1 | 1 | 14-1 | 1 |
| 12-1 | 2 | 13-1 | 2 | 14-1 | 2 |
| 12-1 | 3 | 13-1 | 3 | 14-1 | 3 |
| 12-1 | 4 | 13-1 | 4 | 14-1 | 4 |
| 12-1 | 5 | 13-1 | 5 | 14-1 | 5 |
| 12-1 | 6 | 13-1 | 6 | 14-1 | 6 |
| 12-1 | 7 | 13-1 | 7 | 14-1 | 7 |
| 12-1 | 8 | 13-1 | 8 | 14-1 | 8 |
| 12-1 | 9 | 13-1 | 9 | 14-1 | 9 |
| 12-1 | 10 | 13-1 | 10 | 14-1 | 10 |
| 12-1 | 11 | 13-1 | 11 | 14-1 | 11 |
| 12-1 | 12 | 13-1 | 12 | 14-1 | 12 |
| 12-1 | 13 | 13-1 | 13 | 14-1 | 13 |
| 12-1 | 14 | 13-1 | 14 | 14-1 | 14 |
| 12-1 | 15 | 13-1 | 15 | 14-1 | 15 |
| 12-1 | 16 | 13-1 | 16 | 14-1 | 16 |
| 12-1 | 17 | 13-1 | 17 | 14-1 | 17 |
| 12-1 | 18 | 13-1 | 18 | 14-1 | 18 |
| 12-1 | 19 | 13-1 | 19 | 14-1 | 19 |
| 12-1 | 20 | 13-1 | 20 | 14-1 | 20 |
| 12-1 | 21 | 13-1 | 21 | 14-1 | 21 |
| 12-1 | 22 | 13-1 | 22 | 14-1 | 22 |
| 12-1 | 23 | 13-1 | 23 | 14-1 | 23 |
| 12-1 | 24 | 13-1 | 24 | 14-1 | 24 |
| 12-1 | 25 | 13-1 | 25 | 14-1 | 25 |
| 12-1 | 26 | 13-1 | 26 | 14-1 | 26 |
| 12-1 | 27 | 13-1 | 27 | 14-1 | 27 |
| 12-1 | 28 | 13-1 | 28 | 14-1 | 28 |
| 12-1 | 29 | 13-1 | 29 | 14-1 | 29 |
| 12-1 | 30 | 13-1 | 30 | 14-1 | 30 |
| 12-1 | 31 | 13-1 | 31 | 14-1 | 31 |
| 12-1 | 32 | 13-1 | 32 | 14-1 | 32 |
| 12-1 | 33 | 13-1 | 33 | 14-1 | 33 |
| 12-1 | 34 | 13-1 | 34 | 14-1 | 34 |
| 12-1 | 35 | 13-1 | 35 | 14-1 | 35 |
| 12-1 | 36 | 13-1 | 36 | 14-1 | 36 |
| 12-1 | 37 | 13-1 | 37 | 14-1 | 37 |
| 12-1 | 38 | 13-1 | 38 | 14-1 | 38 |
| 12-1 | 39 | 13-1 | 39 | 14-1 | 39 |
| 12-1 | 40 | 13-1 | 40 | 14-1 | 40 |
| 12-1 | 41 | 13-1 | 41 | 14-1 | 41 |
| 12-1 | 42 | 13-1 | 42 | 11-1 | 42 |
| 12-1 | 43 | 13-1 | 43 | 14-1 | 43 |
| 12-1 | 44 | 13-1 | 44 | 14-1 | 44 |
| 12-1 | 45 | 13-1 | 45 | 14-1 | 45 |
| 12-1 | 46 | 13-1 | 46 | 14-1 | 46 |
| 12-1 | 47 | 13-1 | 47 | 14-1 | 47 |
| 12-1 | 48 | 13-1 | 48 | | |
| 12-1 | 49 | 13-1 | 49 | | |
| 12-1 | 50 | 13-1 | 50 | | |
| 12-1 | 51 | 13-1 | 51 | | |
| 12-1 | 52 | 13-1 | 52 | | |
| 12-1 | 53 | 13-1 | 53 | | |
| 12-1 | 54 | 13-1 | 54 | | |
| 12-1 | 55 | 13-1 | 55 | | |
| 12-1 | 56 | 13-1 | 56 | | |
| 12-1 | 57 | 13-1 | 57 | | |
| 15-1 | 1 | 15-2 | 1 | 15-3 | 1 |
| 15-1 | 2 | 15-2 | 2 | 15-3 | 2 |
| 15-1 | 3 | 15-2 | 3 | 15-3 | 3 |
| 15-1 | 4 | 15-2 | 4 | 15-3 | 4 |
| 15-1 | 5 | 15-2 | 5 | 15-3 | 5 |
| 15-1 | 6 | 15-2 | 6 | 15-3 | 6 |
| 15-1 | 7 | 15-2 | 7 | 15-3 | 7 |
| 15-1 | 8 | 15-2 | 8 | 15-3 | 8 |
| 15-1 | 9 | 15-2 | 9 | 15-3 | 9 |
| 15-1 | 10 | 15-2 | 10 | 15-3 | 10 |
| 15-1 | 11 | 15-2 | 11 | 15-3 | 11 |
| 15-1 | 12 | 15-2 | 12 | 15-3 | 12 |
| 15-1 | 13 | 15-2 | 13 | 15-3 | 13 |
| 15-1 | 14 | 15-2 | 14 | 15-3 | 14 |
| 15-1 | 15 | 15-2 | 15 | 15-3 | 15 |
| 15-1 | 16 | 15-2 | 16 | 15-3 | 16 |
| 15-1 | 17 | 15-2 | 17 | 15-3 | 17 |
| 15-1 | 18 | 15-2 | 18 | 15-3 | 18 |
| 15-1 | 19 | 15-2 | 19 | 15-3 | 19 |
| 15-1 | 20 | 15-2 | 20 | 15-3 | 20 |
| 15-1 | 21 | 15-2 | 21 | 15-3 | 21 |
| 15-1 | 22 | 15-2 | 22 | 15-3 | 22 |
| 15-1 | 23 | 15-2 | 23 | 15-3 | 23 |
| 15-1 | 24 | 15-2 | 24 | 15-3 | 24 |
| 15-1 | 25 | 15-2 | 25 | 15-3 | 25 |
| 15-1 | 26 | 15-2 | 26 | 15-3 | 26 |
| 15-1 | 27 | 15-2 | 27 | 15-3 | 27 |
| 15-1 | 28 | 15-2 | 28 | 15-3 | 28 |
| 15-1 | 29 | 15-2 | 29 | 15-3 | 29 |
| 15-1 | 30 | 15-2 | 30 | 15-3 | 30 |
| 15-1 | 31 | 15-2 | 31 | 15-3 | 31 |
| 15-1 | 32 | 15-2 | 32 | 15-3 | 32 |
| 15-1 | 33 | 15-2 | 33 | 15-3 | 33 |

TABLE 2-continued

Sulfonylurea I' and II''
$A_{z-y}$—$SO_2$—NH—CO—NH—$P_n$ and
$A_{z-y}$—$SO_2$—NH—CO—NH—$T_n$

| $A_{x-y}$ | $P_n/T_n$ | $A_{x-y}$ | $P_n/T_n$ | $A_{x-y}$ | $P_n/T_n$ | $A_{x-y}$ | $P_n/T_n$ | $A_{x-y}$ | $P_n/T_n$ | $A_{x-y}$ | $P_n/T_n$ |
|---|---|---|---|---|---|---|---|---|---|---|---|
| 15-1 | 34 | 15-2 | 34 | 15-3 | 34 | 15-7 | 17 | 15-8 | 17 | 15-9 | 17 |
| 15-1 | 35 | 15-2 | 35 | 15-3 | 35 | 15-7 | 18 | 15-8 | 18 | 15-9 | 18 |
| 15-1 | 36 | 15-2 | 36 | 15-3 | 36 | 15-7 | 19 | 15-8 | 19 | 15-9 | 19 |
| 15-1 | 37 | 15-2 | 37 | 15-3 | 37 | 15-7 | 20 | 15-8 | 20 | 15-9 | 20 |
| 15-1 | 38 | 15-2 | 38 | 15-3 | 38 | 15-7 | 21 | 15-8 | 21 | 15-9 | 21 |
| 15-1 | 39 | 15-2 | 39 | 15-3 | 39 | 15-7 | 22 | 15-8 | 22 | 15-9 | 22 |
| 15-1 | 40 | 15-2 | 40 | 15-3 | 40 | 15-7 | 23 | 15-8 | 23 | 15-9 | 23 |
| 15-1 | 41 | 15-2 | 41 | 15-3 | 41 | 15-7 | 24 | 15-8 | 24 | 15-9 | 24 |
| 15-1 | 42 | 15-2 | 42 | 15-3 | 42 | 15-7 | 25 | 15-8 | 25 | 15-9 | 25 |
| 15-1 | 43 | 15-2 | 43 | 15-3 | 43 | 15-7 | 26 | 15-8 | 26 | 15-9 | 26 |
| 15-1 | 44 | 15-2 | 44 | 15-3 | 44 | 15-7 | 27 | 15-8 | 27 | 15-9 | 27 |
| 15-1 | 45 | 15-2 | 45 | 15-3 | 45 | 15-7 | 28 | 15-8 | 28 | 15-9 | 28 |
| 15-1 | 46 | 15-2 | 46 | 15-3 | 46 | 15-7 | 29 | 15-8 | 29 | 15-9 | 29 |
| 15-1 | 47 | 15-2 | 47 | 15-3 | 47 | 15-7 | 30 | 15-8 | 30 | 15-9 | 30 |
| 15-4 | 1 | 15-5 | 1 | 15-6 | 1 | 15-7 | 31 | 15-8 | 31 | 15-9 | 31 |
| 15-4 | 2 | 15-5 | 2 | 15-6 | 2 | 15-7 | 32 | 15-8 | 32 | 15-9 | 32 |
| 15-4 | 3 | 15-5 | 3 | 15-6 | 3 | 15-7 | 33 | 15-8 | 33 | 15-9 | 33 |
| 15-4 | 4 | 15-5 | 4 | 15-6 | 4 | 15-7 | 34 | 15-8 | 34 | 15-9 | 34 |
| 15-4 | 5 | 15-5 | 5 | 15-6 | 5 | 15-7 | 35 | 15-8 | 35 | 15-9 | 35 |
| 15-4 | 6 | 15-5 | 6 | 15-6 | 6 | 15-7 | 36 | 15-8 | 36 | 15-9 | 36 |
| 15-4 | 7 | 15-5 | 7 | 15-6 | 7 | 15-7 | 37 | 15-8 | 37 | 15-9 | 37 |
| 15-4 | 8 | 15-5 | 8 | 15-6 | 8 | 15-7 | 38 | 15-8 | 38 | 15-9 | 38 |
| 15-4 | 9 | 15-5 | 9 | 15-6 | 9 | 15-7 | 39 | 15-8 | 39 | 15-9 | 39 |
| 15-4 | 10 | 15-5 | 10 | 15-6 | 10 | 15-7 | 40 | 15-8 | 40 | 15-9 | 40 |
| 15-4 | 11 | 15-5 | 11 | 15-6 | 11 | 15-7 | 41 | 15-8 | 41 | 15-9 | 41 |
| 15-4 | 12 | 15-5 | 12 | 15-6 | 12 | 15-7 | 42 | 15-8 | 42 | 15-9 | 42 |
| 15-4 | 13 | 15-5 | 13 | 15-6 | 13 | 15-7 | 43 | 15-8 | 43 | 15-9 | 43 |
| 15-4 | 14 | 15-5 | 14 | 15-6 | 14 | 15-7 | 44 | 15-8 | 44 | 15-9 | 44 |
| 15-4 | 15 | 15-5 | 15 | 15-6 | 15 | 15-7 | 45 | 15-8 | 45 | 15-9 | 45 |
| 15-4 | 16 | 15-5 | 16 | 15-6 | 16 | 15-7 | 46 | 15-8 | 46 | 15-9 | 46 |
| 15-4 | 17 | 15-5 | 17 | 15-6 | 17 | 15-7 | 47 | 15-8 | 47 | 15-9 | 47 |
| 15-4 | 18 | 15-5 | 18 | 15-6 | 18 | 15-10 | 1 | 15-11 | 1 | 15-12 | 1 |
| 15-4 | 19 | 15-5 | 19 | 15-6 | 19 | 15-10 | 2 | 15-11 | 2 | 15-12 | 2 |
| 15-4 | 20 | 15-5 | 20 | 15-6 | 20 | 15-10 | 3 | 15-11 | 3 | 15-12 | 3 |
| 15-4 | 21 | 15-5 | 21 | 15-6 | 21 | 15-10 | 4 | 15-11 | 4 | 15-12 | 4 |
| 15-4 | 22 | 15-5 | 22 | 15-6 | 22 | 15-10 | 5 | 15-11 | 5 | 15-12 | 5 |
| 15-4 | 23 | 15-5 | 23 | 15-6 | 23 | 15-10 | 6 | 15-11 | 6 | 15-12 | 6 |
| 15-4 | 24 | 15-5 | 24 | 15-6 | 24 | 15-10 | 7 | 15-11 | 7 | 15-12 | 7 |
| 15-4 | 25 | 15-5 | 25 | 15-6 | 25 | 15-10 | 8 | 15-11 | 8 | 15-12 | 8 |
| 15-4 | 26 | 15-5 | 26 | 15-6 | 26 | 15-10 | 9 | 15-11 | 9 | 15-12 | 9 |
| 15-4 | 27 | 15-5 | 27 | 15-6 | 27 | 15-10 | 10 | 15-11 | 10 | 15-12 | 10 |
| 15-4 | 28 | 15-5 | 28 | 15-6 | 28 | 15-10 | 11 | 15-11 | 11 | 15-12 | 11 |
| 15-4 | 29 | 15-5 | 29 | 15-6 | 29 | 15-10 | 12 | 15-11 | 12 | 15-12 | 12 |
| 15-4 | 30 | 15-5 | 30 | 15-6 | 30 | 15-10 | 13 | 15-11 | 13 | 15-12 | 13 |
| 15-4 | 31 | 15-5 | 31 | 15-6 | 31 | 15-10 | 14 | 15-11 | 14 | 15-12 | 14 |
| 15-4 | 32 | 15-5 | 32 | 15-6 | 32 | 15-10 | 15 | 15-11 | 15 | 15-12 | 15 |
| 15-4 | 33 | 15-5 | 33 | 15-6 | 33 | 15-10 | 16 | 15-11 | 16 | 15-12 | 16 |
| 15-4 | 34 | 15-5 | 34 | 15-6 | 34 | 15-10 | 17 | 15-11 | 17 | 15-12 | 17 |
| 15-4 | 35 | 15-5 | 35 | 15-6 | 35 | 15-10 | 18 | 15-11 | 18 | 15-12 | 18 |
| 15-4 | 36 | 15-5 | 36 | 15-6 | 36 | 15-10 | 19 | 15-11 | 19 | 15-12 | 19 |
| 15-4 | 37 | 15-5 | 37 | 15-6 | 37 | 15-10 | 20 | 15-11 | 20 | 15-12 | 20 |
| 15-4 | 38 | 15-5 | 38 | 15-6 | 38 | 15-10 | 21 | 15-11 | 21 | 15-12 | 21 |
| 15-4 | 39 | 15-5 | 39 | 15-6 | 39 | 15-10 | 22 | 15-11 | 22 | 15-12 | 22 |
| 15-4 | 40 | 15-5 | 40 | 15-6 | 40 | 15-10 | 23 | 15-11 | 23 | 15-12 | 23 |
| 15-4 | 41 | 15-5 | 41 | 15-6 | 41 | 15-10 | 24 | 15-11 | 24 | 15-12 | 24 |
| 15-4 | 42 | 15-5 | 42 | 15-6 | 42 | 15-10 | 25 | 15-11 | 25 | 15-12 | 25 |
| 15-4 | 43 | 15-5 | 43 | 15-6 | 43 | 15-10 | 26 | 15-11 | 26 | 15-12 | 26 |
| 15-4 | 44 | 15-5 | 44 | 15-6 | 44 | 15-10 | 27 | 15-11 | 27 | 15-12 | 27 |
| 15-4 | 45 | 15-5 | 45 | 15-6 | 45 | 15-10 | 28 | 15-11 | 28 | 15-12 | 28 |
| 15-4 | 46 | 15-5 | 46 | 15-6 | 46 | 15-10 | 29 | 15-11 | 29 | 15-12 | 29 |
| 15-4 | 47 | 15-5 | 47 | 15-6 | 47 | 15-10 | 30 | 15-11 | 30 | 15-12 | 30 |
| 15-7 | 1 | 15-8 | 1 | 15-9 | 1 | 15-10 | 31 | 15-11 | 31 | 15-12 | 31 |
| 15-7 | 2 | 15-8 | 2 | 15-9 | 2 | 15-10 | 32 | 15-11 | 32 | 15-12 | 32 |
| 15-7 | 3 | 15-8 | 3 | 15-9 | 3 | 15-10 | 33 | 15-11 | 33 | 15-12 | 33 |
| 15-7 | 4 | 15-8 | 4 | 15-9 | 4 | 15-10 | 34 | 15-11 | 34 | 15-12 | 34 |
| 15-7 | 5 | 15-8 | 5 | 15-9 | 5 | 15-10 | 35 | 15-11 | 35 | 15-12 | 35 |
| 15-7 | 6 | 15-8 | 6 | 15-9 | 6 | 15-10 | 36 | 15-11 | 36 | 15-12 | 36 |
| 15-7 | 7 | 15-8 | 7 | 15-9 | 7 | 15-10 | 37 | 15-11 | 37 | 15-12 | 37 |
| 15-7 | 8 | 15-8 | 8 | 15-9 | 8 | 15-10 | 38 | 15-11 | 38 | 15-12 | 38 |
| 15-7 | 9 | 15-8 | 9 | 15-9 | 9 | 15-10 | 39 | 15-11 | 39 | 15-12 | 39 |
| 15-7 | 10 | 15-8 | 10 | 15-9 | 10 | 15-10 | 40 | 15-11 | 40 | 15-12 | 40 |
| 15-7 | 11 | 15-8 | 11 | 15-9 | 11 | 15-10 | 41 | 15-11 | 41 | 15-12 | 41 |
| 15-7 | 12 | 15-8 | 12 | 15-9 | 12 | 15-10 | 42 | 15-11 | 42 | 15-12 | 42 |
| 15-7 | 13 | 15-8 | 13 | 15-9 | 13 | 15-10 | 43 | 15-11 | 43 | 15-12 | 43 |
| 15-7 | 14 | 15-8 | 14 | 15-9 | 14 | 15-10 | 44 | 15-11 | 44 | 15-12 | 44 |
| 15-7 | 15 | 15-8 | 15 | 15-9 | 15 | 15-10 | 45 | 15-11 | 45 | 15-12 | 45 |
| 15-7 | 16 | 15-8 | 16 | 15-9 | 16 | 15-10 | 46 | 15-11 | 46 | 15-12 | 46 |

TABLE 2-continued

Sulfonylurea I' and II''
$A_{z-y}-SO_2-NH-CO-NH-P_n$ and
$A_{z-y}-SO_2-NH-CO-NH-T_n$

| $A_{x-y}$ | $P_n/T_n$ | $A_{x-y}$ | $P_n/T_n$ | $A_{x-y}$ | $P_n/T_n$ |
|---|---|---|---|---|---|
| 15-10 | 47 | 15-11 | 47 | 15-12 | 47 |
| 15-13 | 1 | 15-13 | 42 | | |
| 15-13 | 2 | 15-13 | 43 | | |
| 15-13 | 3 | 15-13 | 44 | | |
| 15-13 | 4 | 15-13 | 45 | | |
| 15-13 | 5 | 15-13 | 46 | | |
| 15-13 | 6 | 15-13 | 47 | | |
| 15-13 | 7 | | | | |
| 15-13 | 8 | | | | |
| 15-13 | 9 | | | | |
| 15-13 | 10 | | | | |
| 15-13 | 11 | | | | |
| 15-13 | 12 | | | | |
| 15-13 | 13 | | | | |
| 15-13 | 14 | | | | |
| 15-13 | 15 | | | | |
| 15-13 | 16 | | | | |
| 15-13 | 17 | | | | |
| 15-13 | 18 | | | | |
| 15-13 | 19 | | | | |
| 15-13 | 20 | | | | |
| 15-13 | 21 | | | | |
| 15-13 | 22 | | | | |
| 15-13 | 23 | | | | |
| 15-13 | 24 | | | | |
| 15-13 | 25 | | | | |
| 15-13 | 26 | | | | |
| 15-13 | 27 | | | | |
| 15-13 | 28 | | | | |
| 15-13 | 29 | | | | |
| 15-13 | 30 | | | | |
| 15-13 | 31 | | | | |
| 15-13 | 32 | | | | |
| 15-13 | 33 | | | | |
| 15-13 | 34 | | | | |
| 15-13 | 35 | | | | |
| 15-13 | 36 | | | | |
| 15-13 | 37 | | | | |
| 15-13 | 38 | | | | |
| 15-13 | 39 | | | | |
| 15-13 | 40 | | | | |
| 15-13 | 41 | | | | |
| 16-1 | 1 | 16-2 | 1 | 16-3 | 1 |
| 16-1 | 2 | 16-2 | 2 | 16-3 | 2 |
| 16-1 | 3 | 16-2 | 3 | 16-3 | 3 |
| 16-1 | 4 | 16-2 | 4 | 16-3 | 4 |
| 16-1 | 5 | 16-2 | 5 | 16-3 | 5 |
| 16-1 | 6 | 16-2 | 6 | 16-3 | 6 |
| 16-1 | 7 | 16-2 | 7 | 16-3 | 7 |
| 16-1 | 8 | 16-2 | 8 | 16-3 | 8 |
| 16-1 | 9 | 16-2 | 9 | 16-3 | 9 |
| 16-1 | 10 | 16-2 | 10 | 16-3 | 10 |
| 16-1 | 11 | 16-2 | 11 | 16-3 | 11 |
| 16-1 | 12 | 16-2 | 12 | 16-3 | 12 |
| 16-1 | 13 | 16-2 | 13 | 16-3 | 13 |
| 16-1 | 14 | 16-2 | 14 | 16-3 | 14 |
| 16-1 | 15 | 16-2 | 15 | 16-3 | 15 |
| 16-1 | 16 | 16-2 | 16 | 16-3 | 16 |
| 16-1 | 17 | 16-2 | 17 | 16-3 | 17 |
| 16-1 | 18 | 16-2 | 18 | 16-3 | 18 |
| 16-1 | 19 | 16-2 | 19 | 16-3 | 19 |
| 16-1 | 20 | 16-2 | 20 | 16-3 | 20 |
| 16-1 | 21 | 16-2 | 21 | 16-3 | 21 |
| 16-1 | 22 | 16-2 | 22 | 16-3 | 22 |
| 16-1 | 23 | 16-2 | 23 | 16-3 | 23 |
| 16-1 | 24 | 16-2 | 24 | 16-3 | 24 |
| 16-1 | 25 | 16-2 | 25 | 16-3 | 25 |
| 16-1 | 26 | 16-2 | 26 | 16-3 | 26 |
| 16-1 | 27 | 16-2 | 27 | 16-3 | 27 |
| 16-1 | 28 | 16-2 | 28 | 16-3 | 28 |
| 16-1 | 29 | 16-2 | 29 | 16-3 | 29 |
| 16-1 | 30 | 16-2 | 30 | 16-3 | 30 |
| 16-1 | 31 | 16-2 | 31 | 16-3 | 31 |
| 16-1 | 32 | 16-2 | 32 | 16-3 | 32 |
| 16-1 | 33 | 16-2 | 33 | 16-3 | 33 |
| 16-1 | 34 | 16-2 | 34 | 16-3 | 34 |
| 16-1 | 35 | 16-2 | 35 | 16-3 | 35 |
| 16-1 | 36 | 16-2 | 36 | 16-3 | 36 |
| 16-1 | 37 | 16-2 | 37 | 16-3 | 37 |
| 16-1 | 38 | 16-2 | 38 | 16-3 | 38 |
| 16-1 | 39 | 16-2 | 39 | 16-3 | 39 |
| 16-1 | 40 | 16-2 | 40 | 16-3 | 40 |
| 16-1 | 41 | 16-2 | 41 | 16-3 | 41 |
| 16-1 | 42 | 16-2 | 42 | 16-3 | 42 |
| 16-1 | 43 | 16-2 | 43 | 16-3 | 43 |
| 16-1 | 44 | 16-2 | 44 | 16-3 | 44 |
| 16-1 | 45 | 16-2 | 45 | 16-3 | 45 |
| 16-1 | 46 | 16-2 | 46 | 16-3 | 46 |
| 16-1 | 47 | 16-2 | 47 | 16-3 | 47 |
| 16-1 | 48 | 16-2 | 48 | 16-3 | 48 |
| 16-1 | 49 | 16-2 | 49 | 16-3 | 49 |
| 16-1 | 50 | 16-2 | 50 | 16-3 | 50 |
| 16-1 | 51 | 16-2 | 51 | 16-3 | 51 |
| 16-1 | 52 | 16-2 | 52 | 16-3 | 52 |
| 16-1 | 53 | 16-2 | 53 | 16-3 | 53 |
| 16-1 | 54 | 16-2 | 54 | 16-3 | 54 |
| 16-1 | 55 | 16-2 | 55 | 16-3 | 55 |
| 16-1 | 56 | 16-2 | 56 | 16-3 | 56 |
| 16-1 | 57 | 16-2 | 57 | 16-3 | 57 |
| 16-4 | 1 | 16-5 | 1 | 16-6 | 1 |
| 16-4 | 2 | 16-5 | 2 | 16-6 | 2 |
| 16-4 | 3 | 16-5 | 3 | 16-6 | 3 |
| 16-4 | 4 | 16-5 | 4 | 16-6 | 4 |
| 16-4 | 5 | 16-5 | 5 | 16-6 | 5 |
| 16-4 | 6 | 16-5 | 6 | 16-6 | 6 |
| 16-4 | 7 | 15-5 | 7 | 16-6 | 7 |
| 16-4 | 8 | 16-5 | 8 | 16-6 | 8 |
| 16-4 | 9 | 16-5 | 9 | 16-6 | 9 |
| 16-4 | 10 | 16-5 | 10 | 16-6 | 10 |
| 16-4 | 11 | 16-5 | 11 | 16-6 | 11 |
| 16-4 | 12 | 16-5 | 12 | 16-6 | 12 |
| 16-4 | 13 | 16-5 | 13 | 16-6 | 13 |
| 16-4 | 14 | 16-5 | 14 | 16-6 | 14 |
| 16-4 | 15 | 16-5 | 15 | 16-6 | 15 |
| 16-4 | 16 | 16-5 | 16 | 16-6 | 16 |
| 16-4 | 17 | 16-5 | 17 | 16-6 | 17 |
| 16-4 | 18 | 16-5 | 18 | 16-6 | 18 |
| 16-4 | 19 | 16-5 | 19 | 16-6 | 19 |
| 16-4 | 20 | 16-5 | 20 | 16-6 | 20 |
| 16-4 | 21 | 16-5 | 21 | 16-6 | 21 |
| 16-4 | 22 | 16-5 | 22 | 16-6 | 22 |
| 16-4 | 23 | 16-5 | 23 | 16-6 | 23 |
| 16-4 | 24 | 16-5 | 24 | 16-6 | 24 |
| 16-4 | 25 | 16-5 | 25 | 16-6 | 25 |
| 16-4 | 26 | 16-5 | 26 | 16-6 | 26 |
| 16-4 | 27 | 16-5 | 27 | 16-6 | 27 |
| 16-4 | 28 | 16-5 | 28 | 16-6 | 28 |
| 16-4 | 29 | 16-5 | 29 | 16-6 | 29 |
| 16-4 | 30 | 16-5 | 30 | 16-6 | 30 |
| 16-4 | 31 | 16-5 | 31 | 16-6 | 31 |
| 16-4 | 32 | 16-5 | 32 | 16-6 | 32 |
| 16-4 | 33 | 16-5 | 33 | 16-6 | 33 |
| 16-4 | 34 | 16-5 | 34 | 16-6 | 34 |
| 16-4 | 35 | 16-5 | 35 | 16-6 | 35 |
| 16-4 | 36 | 16-5 | 36 | 16-6 | 36 |
| 16-4 | 37 | 16-5 | 37 | 16-6 | 37 |
| 16-4 | 38 | 16-5 | 38 | 16-6 | 38 |
| 16-4 | 39 | 16-5 | 39 | 16-6 | 39 |
| 16-4 | 40 | 16-5 | 40 | 16-6 | 40 |
| 16-4 | 41 | 16-5 | 41 | 16-6 | 41 |
| 16-4 | 42 | 16-5 | 42 | 16-6 | 42 |
| 16-4 | 43 | 16-5 | 43 | 16-6 | 43 |
| 16-4 | 44 | 16-5 | 44 | 16-6 | 44 |
| 16-4 | 45 | 16-5 | 45 | 16-6 | 45 |
| 16-4 | 46 | 16-5 | 46 | 16-6 | 46 |
| 16-4 | 47 | 16-5 | 47 | 16-6 | 47 |
| 16-4 | 48 | 16-5 | 48 | 16-6 | 48 |
| 16-4 | 49 | 16-5 | 49 | 16-6 | 49 |
| 16-4 | 50 | 16-5 | 50 | 16-6 | 50 |
| 16-4 | 51 | 16-5 | 51 | 16-6 | 51 |
| 16-4 | 52 | 16-5 | 52 | 16-6 | 52 |
| 16-4 | 53 | 16-5 | 53 | 16-6 | 53 |
| 16-4 | 54 | 16-5 | 54 | 16-6 | 54 |
| 16-4 | 55 | 16-5 | 55 | 16-6 | 55 |

TABLE 2-continued

Sulfonylurea I' and II''
$A_{z-y}$—$SO_2$—NH—CO—NH—$P_n$ and
$A_{z-y}$—$SO_2$—NH—CO—NH—$T_n$

| $A_{x-y}$ | $P_n/T_n$ | $A_{x-y}$ | $P_n/T_n$ | $A_{x-y}$ | $P_n/T_n$ |
|---|---|---|---|---|---|
| 16-4 | 56 | 16-5 | 56 | 16-6 | 56 |
| 16-4 | 57 | 16-5 | 57 | 16-6 | 57 |
| 16-7 | 1 | 16-8 | 1 | 16-9 | 1 |
| 16-7 | 2 | 16-8 | 2 | 16-9 | 2 |
| 16-7 | 3 | 16-8 | 3 | 16-9 | 3 |
| 16-7 | 4 | 16-8 | 4 | 16-9 | 4 |
| 16-7 | 5 | 16-8 | 5 | 16-9 | 5 |
| 16-7 | 6 | 16-8 | 6 | 16-9 | 6 |
| 16-7 | 7 | 16-8 | 7 | 16-9 | 7 |
| 16-7 | 8 | 16-8 | 8 | 16-9 | 8 |
| 16-7 | 9 | 16-8 | 9 | 16-9 | 9 |
| 16-7 | 10 | 16-8 | 10 | 16-9 | 10 |
| 16-7 | 11 | 16-8 | 11 | 16-9 | 11 |
| 16-7 | 12 | 16-8 | 12 | 16-9 | 12 |
| 16-7 | 13 | 16-8 | 13 | 16-9 | 13 |
| 16-7 | 14 | 16-8 | 14 | 16-9 | 14 |
| 16-7 | 15 | 16-8 | 15 | 16-9 | 15 |
| 16-7 | 16 | 16-8 | 16 | 16-9 | 16 |
| 16-7 | 17 | 16-8 | 17 | 16-9 | 17 |
| 16-7 | 18 | 16-8 | 18 | 16-9 | 18 |
| 16-7 | 19 | 16-8 | 19 | 16-9 | 19 |
| 16-7 | 20 | 16-8 | 20 | 16-9 | 20 |
| 16-7 | 21 | 16-8 | 21 | 16-9 | 21 |
| 16-7 | 22 | 16-8 | 22 | 16-9 | 22 |
| 16-7 | 23 | 16-8 | 23 | 16-9 | 23 |
| 16-7 | 24 | 16-8 | 24 | 16-9 | 24 |
| 16-7 | 25 | 16-8 | 25 | 16-9 | 25 |
| 16-7 | 26 | 16-8 | 26 | 16-9 | 26 |
| 16-7 | 27 | 16-8 | 27 | 16-9 | 27 |
| 16-7 | 28 | 16-8 | 28 | 16-9 | 28 |
| 16-7 | 29 | 16-8 | 29 | 16-9 | 29 |
| 16-7 | 30 | 16-8 | 30 | 16-9 | 30 |
| 16-7 | 31 | 16-8 | 31 | 16-9 | 31 |
| 16-7 | 32 | 16-8 | 32 | 16-9 | 32 |
| 16-7 | 33 | 16-8 | 33 | 16-9 | 33 |
| 16-7 | 34 | 16-8 | 34 | 16-9 | 34 |
| 16-7 | 35 | 16-8 | 35 | 16-9 | 35 |
| 16-7 | 36 | 16-8 | 36 | 16-9 | 36 |
| 16-7 | 37 | 16-8 | 37 | 16-9 | 37 |
| 16-7 | 38 | 16-8 | 38 | 16-9 | 38 |
| 16-7 | 39 | 16-8 | 39 | 16-9 | 39 |
| 16-7 | 40 | 16-8 | 40 | 16-9 | 40 |
| 16-7 | 41 | 16-8 | 41 | 16-9 | 41 |
| 16-7 | 42 | 16-8 | 42 | 16-9 | 42 |
| 16-7 | 43 | 16-8 | 43 | 16-9 | 43 |
| 16-7 | 44 | 16-8 | 44 | 16-9 | 44 |
| 16-7 | 45 | 16-8 | 45 | 16-9 | 45 |
| 16-7 | 46 | 16-8 | 46 | 16-9 | 46 |
| 16-7 | 47 | 16-8 | 47 | 16-9 | 47 |
| 16-7 | 48 | 16-8 | 48 | 16-9 | 48 |
| 16-7 | 49 | 16-8 | 49 | 16-9 | 49 |
| 16-7 | 50 | 16-8 | 50 | 16-9 | 50 |
| 16-7 | 51 | 16-8 | 51 | 16-9 | 51 |
| 16-7 | 52 | 16-8 | 52 | 16-9 | 52 |
| 16-7 | 53 | 16-8 | 53 | 16-9 | 53 |
| 16-7 | 54 | 16-8 | 54 | 16-9 | 54 |
| 16-7 | 55 | 16-8 | 55 | 16-9 | 55 |
| 16-7 | 56 | 16-8 | 56 | 16-9 | 56 |
| 16-7 | 57 | 16-8 | 57 | 16-9 | 57 |
| 16-10 | 1 | 16-11 | 1 | 16-12 | 1 |
| 16-10 | 2 | 16-11 | 2 | 16-12 | 2 |
| 16-10 | 3 | 16-11 | 3 | 16-12 | 3 |
| 16-10 | 4 | 16-11 | 4 | 16-12 | 4 |
| 16-10 | 5 | 16-11 | 5 | 16-12 | 5 |
| 16-10 | 6 | 16-11 | 6 | 16-12 | 6 |
| 16-10 | 7 | 16-11 | 7 | 16-12 | 7 |
| 16-10 | 8 | 16-11 | 8 | 16-12 | 8 |
| 16-10 | 9 | 16-11 | 9 | 16-12 | 9 |
| 16-10 | 10 | 16-11 | 10 | 16-12 | 10 |
| 16-10 | 11 | 16-11 | 11 | 16-12 | 11 |
| 16-10 | 12 | 16-11 | 12 | 16-12 | 12 |
| 16-10 | 13 | 16-11 | 13 | 16-12 | 13 |
| 16-10 | 14 | 16-11 | 14 | 16-12 | 14 |
| 16-10 | 15 | 16-11 | 15 | 16-12 | 15 |
| 16-10 | 16 | 16-11 | 16 | 16-12 | 16 |
| 16-10 | 17 | 16-11 | 17 | 16-12 | 17 |
| 16-10 | 18 | 16-11 | 18 | 16-12 | 18 |
| 16-10 | 19 | 16-11 | 19 | 16-12 | 19 |
| 16-10 | 20 | 16-11 | 20 | 16-12 | 20 |
| 16-10 | 21 | 16-11 | 21 | 16-12 | 21 |
| 16-10 | 22 | 16-11 | 22 | 16-12 | 22 |
| 16-10 | 23 | 16-11 | 23 | 16-12 | 23 |
| 16-10 | 24 | 16-11 | 24 | 16-12 | 24 |
| 16-10 | 25 | 16-11 | 25 | 16-12 | 25 |
| 16-10 | 26 | 16-11 | 26 | 16-12 | 26 |
| 16-10 | 27 | 16-11 | 27 | 16-12 | 27 |
| 16-10 | 28 | 16-11 | 28 | 16-12 | 28 |
| 16-10 | 29 | 16-11 | 29 | 16-12 | 29 |
| 16-10 | 30 | 16-11 | 30 | 16-12 | 30 |
| 16-10 | 31 | 16-11 | 31 | 16-12 | 31 |
| 16-10 | 32 | 16-11 | 32 | 16-12 | 32 |
| 16-10 | 33 | 16-11 | 33 | 16-12 | 33 |
| 16-10 | 34 | 16-11 | 34 | 16-12 | 34 |
| 16-10 | 35 | 16-11 | 35 | 16-12 | 35 |
| 16-10 | 36 | 16-11 | 36 | 16-12 | 36 |
| 16-10 | 37 | 16-11 | 37 | 16-12 | 37 |
| 16-10 | 38 | 16-11 | 38 | 16-12 | 38 |
| 16-10 | 39 | 16-11 | 39 | 16-12 | 39 |
| 16-10 | 40 | 16-11 | 40 | 16-12 | 40 |
| 16-10 | 41 | 16-11 | 41 | 16-12 | 41 |
| 16-10 | 42 | 16-11 | 42 | 16-12 | 42 |
| 16-10 | 43 | 16-11 | 43 | 16-12 | 43 |
| 16-10 | 44 | 16-11 | 44 | 16-12 | 44 |
| 16-10 | 45 | 16-11 | 45 | 16-12 | 45 |
| 16-10 | 46 | 16-11 | 46 | 16-12 | 46 |
| 16-10 | 47 | 16-11 | 47 | 16-12 | 47 |
| 16-10 | 48 | 16-11 | 48 | 16-12 | 48 |
| 16-10 | 49 | 16-11 | 49 | 16-12 | 49 |
| 16-10 | 50 | 16-11 | 50 | 16-12 | 50 |
| 16-10 | 51 | 16-11 | 51 | 16-12 | 51 |
| 16-10 | 52 | 16-11 | 52 | 16-12 | 52 |
| 16-10 | 53 | 16-11 | 53 | 16-12 | 53 |
| 16-10 | 54 | 16-11 | 54 | 16-12 | 54 |
| 16-10 | 55 | 16-11 | 55 | 16-12 | 55 |
| 16-10 | 56 | 16-11 | 56 | 16-12 | 56 |
| 16-10 | 57 | 16-11 | 57 | 16-12 | 57 |
| 16-13 | 1 | 16-13 | 34 | | |
| 16-13 | 2 | 16-13 | 35 | | |
| 16-13 | 3 | 16-13 | 36 | | |
| 16-13 | 4 | 16-13 | 37 | | |
| 16-13 | 5 | 16-13 | 38 | | |
| 16-13 | 6 | 16-13 | 39 | | |
| 16-13 | 7 | 16-13 | 40 | | |
| 16-13 | 8 | 16-13 | 41 | | |
| 16-13 | 9 | 16-13 | 42 | | |
| 16-13 | 10 | 16-13 | 43 | | |
| 16-13 | 11 | 16-13 | 44 | | |
| 16-13 | 12 | 16-13 | 45 | | |
| 16-13 | 13 | 16-13 | 46 | | |
| 16-13 | 11 | 16-13 | 47 | | |
| 16-13 | 15 | 16-13 | 48 | | |
| 16-13 | 16 | 16-13 | 49 | | |
| 16-13 | 17 | 16-13 | 50 | | |
| 16-13 | 18 | 16-13 | 51 | | |
| 16-13 | 19 | 16-13 | 52 | | |
| 16-13 | 20 | 16-13 | 53 | | |
| 16-13 | 21 | 16-13 | 54 | | |
| 16-13 | 22 | 16-13 | 55 | | |
| 16-13 | 23 | 16-13 | 56 | | |
| 16-13 | 24 | 16-13 | 57 | | |
| 16-13 | 25 | | | | |
| 16-13 | 26 | | | | |
| 16-13 | 27 | | | | |
| 16-13 | 28 | | | | |
| 16-13 | 29 | | | | |
| 16-13 | 30 | | | | |
| 16-13 | 31 | | | | |
| 16-13 | 32 | | | | |

TABLE 2-continued

Sulfonylurea I' and II"
$A_{z-y}-SO_2-NH-CO-NH-P_n$ and
$A_{z-y}-SO_2-NH-CO-NH-T_n$

| $A_{x-y}$ | $P_n/T_n$ | $A_{x-y}$ | $P_n/T_n$ | $A_{x-y}$ | $P_n/T_n$ |
|---|---|---|---|---|---|
| 16-13 | 33 | | | | |

*The combnation $A_{x-y} = 1\text{-}1$ and $P_nT_2 = 1$ represents the sulfonylureas

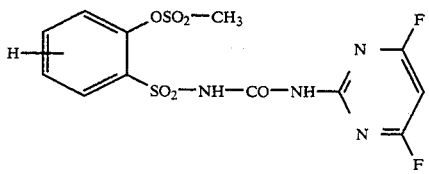

and

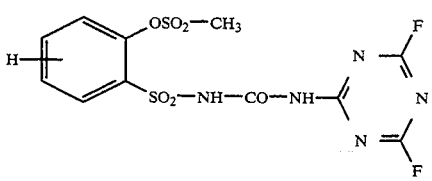

The remaining combinations of numbers are simply to be assigned to the associated sulfonylurea derivatives in a similar manner.

USE EXAMPLES

The herbicidal action of the sulfonylurea derivatives of the formula I was demonstrated by greenhouse experiments.

The culture vessels used were plastic flower pots containing loamy sand with about 3.0% of humus as a substrate. The seeds of the test plants were sown separately according to species.

In the preemergence treatment, the active ingredients suspended or emulsified in water were applied directly after sowing, by means of finely distributing nozzles. The vessels were lightly watered in order to promote germination and growth and then covered with transparent plastic covers until the plants had begun to grow. This covering ensures uniform germination of the test plants, unless this has been adversely affected by the active ingredients.

For the purpose of the postemergence treatment, the test plants were treated with the active ingredients suspended or emulsified in water only at a height of growth of from 3 to 15 cm, depending on the form of growth. For this purpose, the test plants were either sown directly and grown in the same vessels, or they were first grown separately as seedlings and transplanted into the test vessels a few days before the treatment. The application rate for the postemergence treatment was 0.015 kg/ha of active ingredient.

The plants were kept at 10°–25° C. or 20°–35° C., depending on the species. The test period extended over 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal growth.

The plants used in the greenhouse experiments consisted of the following species:

| Botanical name | Common name |
|---|---|
| Chrysanthemum | |
| Sinapis alba | white mustard |
| Stellaria media | chickweed |
| Xanthium pennsylvanicum | common cocklebur |
| Triticum aestivum | winter wheat |
| Zea mays | corn |

Using 0.015 kg/ha of active ingredient by the postemergence method, undesirable broad-leaved plants can be very readily controlled with Examples 1 and 5, which are also tolerated by the example crops wheat and corn.

At an application rate of 0.5 kg/ha in the postemergence method, compound 14 has a very good herbicidal action against the undesirable plants Amaranthus retroflexus, Galium aparine and Ceantaurea cyanus.

In the comparative examples below, the compound A disclosed in EP A 44 212 and the compound B embraced by the general claim stated there were compared with Example No. 1.

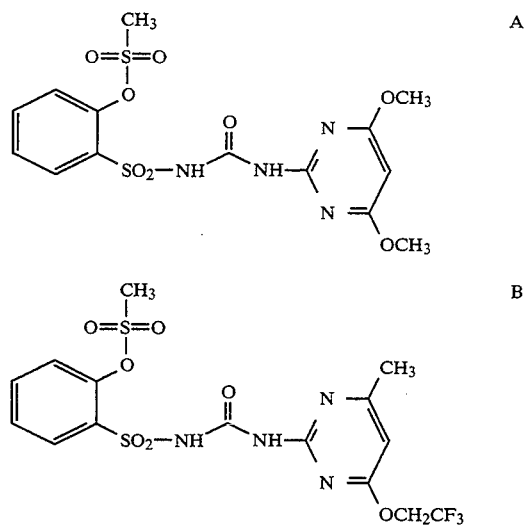

The experimental results which are summarized in Tables 2 and 3 clearly show the surprisingly high selectivity of the claimed compound compared with the comparative substances in conjunction with very good herbicidal activity.

TABLE 2

Examples for the control of undesirable broad-leaved plants and toleration by an example crop in the case of postemergence application of 0.015 and 0.008 kg of a.i./ha in the greenhouse

| | Damage in % | | | |
|---|---|---|---|---|
| | Example 1 | | Example A | |
| Test plants | 0.015 kg/ha | 0.008 kg/ha | 0.015 kg/ha | 0.008 kg/ha |
| Zea mays undesirable plants: | 20 | 20 | 75 | 75 |
| Xanthium pennsylvanicum | 90 | 90 | 80 | 80 |
| Chrysanthemum | 100 | 100 | 100 | 100 |
| Solanum nigrum | 100 | 98 | 75 | 20 |

TABLE 3

Examples for the control of undesirable broad-leaved plants and toleration by an example crop in the case of postemergence application of 0.015 and 0.008 kg of a.i./ha in the greenhouse

| Test plants | Damage in % | | | |
|---|---|---|---|---|
| | Example 1 | | Example A | |
| | 0.015 kg/ha | 0.008 kg/ha | 0.015 kg/ha | 0.008 kg/ha |
| *Zea mays* undesirable plants: | 20 | 20 | 70 | 70 |
| *Xanthium pennsylvanicum* | 90 | 90 | 50 | 50 |
| *Chrysanthemum* | 100 | 100 | 85 | 70 |
| *Solanum nigrum* | 100 | 98 | 15 | 10 |

We claim:

1. A substituted sulfonylurea derivative of the formula I

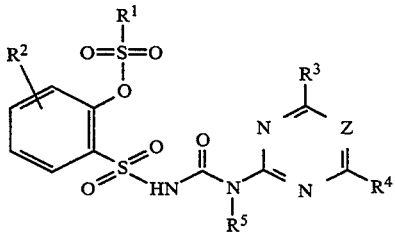

where $R^1$ is $C_1$–$C_4$-alkyl which may carry up to three of the following radicals: halogen or $C_1$- or $C_2$-alkoxy; $C_2$- or $C_3$-alkenyl; propargyl; $C_1$–$C_3$-alkylamino or di-$C_1$–$C_4$-alkylamino; or phenyl which may carry up to three of the following radicals: halogen, $C_1$–$C_4$-alkyl or $C_1$- or $C_2$-alkoxy;

$R^2$ is hydrogen, halogen, methyl, methoxy or ethoxy, each of which may carry from 1 to 3 halogen atoms, or $C_1$- or $C_2$-alkylsulfonyl, nitro or cyano;

$R^3$ is trifluoromethoxy, bromodifluoromethoxy, chlorodifluoromethoxy or fluorine;

$R^4$ is halogen, methyl, ethyl, $C_1$- or $C_2$-haloalkyl, $C_1$- or $C_2$-haloalkoxy, methoxy, ethoxy, methylamino or dimethylamino;

$R^5$ is hydrogen, $C_1$–$C_3$-alkyl, $C_2$- or $C_3$-alkenyl or $C_3$- or $C_4$-alkynyl and Z is CH or an agriculturally useful salt thereof.

2. A substituted sulfonylurea derivative of the formula I as claimed in claim 1, where $R^1$ to $R^4$ and Z have the meanings stated in claim 1 and $R^5$ is hydrogen or methyl.

3. A substituted sulfonylurea derivative of the formula I as claimed in claim 1, where $R^1$ is $C_1$–$C_4$-alkyl which may be monosubstituted to trisubstituted by halogen or $C_1$- or $C_2$-alkoxy or $R^1$ is propargyl or $C_2$- or $C_3$-alkenyl, $R^5$ is hydrogen or methyl and $R^2$ to $R^4$ and Z have the meanings stated in claim 1.

4. A substituted sulfonylurea derivative of the formula I as claimed in claim 1, where $R^1$ is $C_1$–$C_3$-alkylamino or di-$C_1$–$C_4$-alkylamino, $R^5$ is hydrogen or methyl and $R^2$ to $R^4$ and Z have the meanings stated in claim 1.

5. A substituted sulfonylurea derivative of the formula I as claimed in claim 1, where $R^1$ is phenyl which may carry from 1 to 3 of the following radicals: halogen, $C_1$–$C_4$-alkyl, methoxy or ethoxy, $R^5$ is hydrogen or methyl and $R^2$ to $R^4$ and Z have the meanings stated in claim 1.

6. A substituted sulfonylurea derivative of the formula I as claimed in claim 1, wherein $R^1$ is $C_1$–$C_4$-alkyl which may carry from 1 to 3 halogen atoms or $R^1$ is propargyl, $C_2$- or $C_3$-alkenyl, methylamino or dimethylamino, $R^3$ is trifluoromethoxy, chlorodifluoromethoxy or fluorine, $R^5$ is hydrogen or methyl and $R^2$, $R^4$ and Z have the meanings stated in claim 1.

7. A substituted sulfonylurea derivative of the formula I as claimed in claim 1, wherein $R^1$ is $C_1$–$C_4$-alkyl which may carry from 1 to 3 halogen atoms or $R^1$ is propargyl, $C_2$- or $C_3$-alkenyl, methylamino or dimethylamino, $R^3$ is trifluoromethoxy, chlorodifluoromethoxy or fluorine, $R^4$ is methoxy, $R^5$ is hydrogen or methyl and $R^2$ and Z have the meanings stated in claim 1.

8. A method for controlling undesirable plant growth in a corn habitat comprising treating the corn habitat with a herbicidal amount of a sulfonylurea derivative of the formula I as claimed in claim 1 or of a salt thereof.

* * * * *